(12) United States Patent
Matz et al.

(10) Patent No.: US 7,230,080 B2
(45) Date of Patent: Jun. 12, 2007

(54) FLUORESCENT AND COLORED PROTEINS, AND POLYNUCLEOTIDES THAT ENCODE THESE PROTEINS

(75) Inventors: Mikhail Vladimirovitch Matz, Palm Coast, FL (US); Naila Omar Khayyam Alieva, Palm Coast, FL (US); Karen Ann Konzen, St. Augustine, FL (US); Steven Field, Daytona Beach, FL (US); Anya Salih, Waterloo (AU)

(73) Assignees: University of Florida Research Foundation, Inc., Gainesville, FL (US); University of Sydney, Sydney (AU)

( * ) Notice: Subject to any disclaimer, the term of this patent is extended or adjusted under 35 U.S.C. 154(b) by 0 days.

(21) Appl. No.: 11/058,952

(22) Filed: Feb. 16, 2005

(65) Prior Publication Data

US 2006/0183133 A1 Aug. 17, 2006

(51) Int. Cl.
*C07K 1/00* (2006.01)
*C12N 15/00* (2006.01)
*C12N 9/12* (2006.01)
*C12N 1/20* (2006.01)

(52) U.S. Cl. .................. 530/350; 435/69.1; 435/252.3; 435/320.1

(58) Field of Classification Search .................. 530/350; 435/69.1, 252.3, 320.1
See application file for complete search history.

(56) References Cited

U.S. PATENT DOCUMENTS

| | | | |
|---|---|---|---|
| 5,268,463 A | 12/1993 | Jefferson | |
| 5,491,084 A | 2/1996 | Chalfie et al. | |
| 5,639,663 A | 6/1997 | Crosby et al. | |
| 5,804,387 A | 9/1998 | Cormack et al. | |
| 5,874,304 A | 2/1999 | Zolotukhin et al. | |
| 5,919,445 A | 7/1999 | Chao | |
| 5,958,713 A | 9/1999 | Thastrup et al. | |
| 5,968,738 A | 10/1999 | Anderson et al. | |
| 5,968,750 A | 10/1999 | Zolotukhin et al. | |
| 5,976,796 A | 11/1999 | Szalay et al. | |
| 5,985,577 A | 11/1999 | Bulinski | |
| 6,020,192 A | 2/2000 | Muzyczka et al. | |
| 6,066,476 A | 5/2000 | Tsien et al. | |
| 6,455,759 B1 | 9/2002 | Vierstra et al. | |

OTHER PUBLICATIONS

Anderluh G. et al., "Cloning, Sequencing, and Expression of Equinatoxin II," *Biochemical and Biophysical Research Communications*, 1996, 220:437-442.

Ando, R. et al., "An Optical Marker Based on the UV-Induced Green-to-Red Photoconversion of a Fluorescent Protein," *Proceedings of the National Academy of Sciences* (2002), 99(20):12651-12656.

Chudakov D. M. et al., "Kindling Fluorescent Proteins for Precise in vivo Photolableing," *Nature Biotechnology*, 2003, 21:191-194.

(Continued)

*Primary Examiner*—Maryam Monshipouri
(74) *Attorney, Agent, or Firm*—Saliwanchik, Lloyd & Saliwanchik

(57) ABSTRACT

The subject invention provides new fluorescent and/or colored proteins, and polynucleotide sequences that encode these proteins. The subject invention further provides materials and methods useful for expressing these detectable proteins in biological systems.

2 Claims, 21 Drawing Sheets

OTHER PUBLICATIONS

Eichinger L. et al., "Dictyostelium as Model System for Studies of the Actin Cytoskeleton by Molecular Genetics," *Microscopy Research and Technique*, 1999, 47:124-134.

Falk M. M. et al., "High Resolution, Fluorescent Deconvolution Microscopy and Tagging With the Autofluorescent Tracers CFP, GFP, and YFP to Study the Structural Composition of Gap Junctions in Living Cells," *Microscopy Research and Technique*, 2001, 52:251-262.

Fradkov A. F. et al., "Novel Fluorescent Protein From Discosoma Coral and Its Mutants Possesses a Unique Far-Red Fluorescent," *FEBS Letters*, 2000, 479:127-130.

Gurskaya N. G. et al., "GFP-like Chromosomes as a Source of Far-Red Fluorescent Proteins," *FEBS Letters*, 2001, 507:16-20.

Gurskaya N. G. et al., "Color Transitions in Coral's Fluorescent Proteins by Site-Directed Mutagenesis," *BMC Biochemistry*, 2001, 2:6.

Hanson M. R. et al., "GFP Imaging: Methodology and Application to Investigate Cellular Compartmentation in plants," *Journal of Experimental Botany*, 2001, 52:529-539.

Hillisch A. et al., "Recent Advances in FRET: Distance Determination in Protein-DNA Complexes," *Current Opinion in Structural Biology*, 2001, 11:201-207.

Houtsmuller A. B. et al., "Macromolecular Dynamics in Living Cell Nuclei Revealed by Fluorescent Redistribution After Photobleaching," *Histochem Cell Biol*, 2001, 115:13-21.

Kallal L. et al., "Using Grenn Fluorescent Proteins to Study G-Protein-Coupled Receptor Localization Trafficking," *Trends Pharmacol Sci*, 21:175-180, 2000.

Labas Y. A. et al., "Diversity and Evolution of the Green Fluorescent Protein Family," *Proc Natl Acad Sci USA*, 2002, 99:4256-4261.

Laird D. W. et al., "Comparative Analysis and Application of Fluorescent Protein-Tagged Connexins," *Microscopy and Research Technique*, 2001, 52:263-272.

Lukyanov K. A. et al., "Natural Animal Coloration Can Be Determined by a Nonfluorescent Green Fluorescent Protein Homolog," *J Biol Chemistry*, 2000, 275(34):25879-25882.

Macek, P. et al., "Intrinsic Tryptoohan Fluorescence of Equinatoxin II, a Pore-Forming Polypeptide From the Sea Anemone *Actinia equina* L, Monitors Its Interaction With Lipid Membranes," *European Journal of Biochemistry* (1995), 234:329-335.

Martynov V. I. et al., "Alternative Cyclization in GFP-like Proteins Family," *J Biol Chem*, 2001, 276:21012-6.

Matz M. V. et al, "Family of the Green Fluorescent Protein: Journey to the End of the Rainbow," *Bioessays*, 2002, 24:953-959.

Matz M. V. et al., "Fluorescent Proteins From Nonbioluminescent Anthozoa Species," *Nature Biotechnol*, 1999, 17:969-973.

Patterson G. H. et al., "A Photoactivatable GFP for Selective Photolabeling of Proteins and Cells," *Science*, 2002, 297:1873-1877.

Pollok B. A. and Roger Heim, "Using GFP in FRET-based Applications," *Cell Biology*, 1999, 9:57-60.

Reits E. et al., "From Fixed to FRAP: Measuring Protein Mobility and Activity in Living Cells," *Nature Cell Biology*, 2001, 3:E145-147.

Terskikh A. et al., "Fluorescent Timer: Protein That Changes Color With Time," *Science*, 2000, 290:1585-8.

Tsien R. Y., "The Green Fluorescent Protein," *Annu Rev Biochem*, 1998, 67:509-544.

Tsien R. Y., "Rosy Dawn for Fluorescent Proteins," *Nat Biotech*, 1999, 17:956-957.

Verkhusha V. V., et al., "An Enhanced Mutant of Red Fluorescent Protein DsRed for Developmental Timer of Neural Fiber Bundle Formation," *Journal of Biological Chemistry*, 2001, 276:29621-29624.

Ward W. W. et al., "An Energy Transfer Protein in Coelenterate Bioluminescence," *J Biol Chem*, 1979, 254:781-788.

Yanushevich Y. G. et al., "A Strategy for the Generation of Non-Aggregating Mutants of Anthozoa Fluorescent Proteins," *FEBS Letters*, 2002, 511:11-14.

Yarbrough D. et al., "Refined Crystal Structure of DsRed, a Red Fluorescent Protein From Coral, at 2.0-A Resolution," *Proc Natl Acad Sci USA*, 2001, 98:462-7.

SEQUENCE LISTING

```
<160> NUMBER OF SEQ ID NOS: 44

<210> SEQ ID NO 1
<211> LENGTH: 27
<212> TYPE: DNA
<213> ORGANISM: Artificial sequence
<220> FEATURE:
<223> OTHER INFORMATION: 5' heel of upstream primer used according to
      subject invention

<400> SEQUENCE: 1
ttgattgatt gaaggagaaa tatcatg                                           27

<210> SEQ ID NO 2
<211> LENGTH: 24
<212> TYPE: DNA
<213> ORGANISM: Artificial sequence
<220> FEATURE:
<223> OTHER INFORMATION: 5' heel of a downstream primer used according
      to the subject invention

<400> SEQUENCE: 2
ttattagtga tggtgatggt gatg                                              24

<210> SEQ ID NO 3
<211> LENGTH: 720
<212> TYPE: DNA
<213> ORGANISM: Montipora millepora
<220> FEATURE:
<221> NAME/KEY: misc_feature
<222> LOCATION: (1)..(24)
<223> OTHER INFORMATION: Part of the sequence that has been artificially
      added during the
      cloning process to facilitate gene expression in E. coli.
<220> FEATURE:
<221> NAME/KEY: misc_feature
```

<222> LOCATION: (712)..(720)
<223> OTHER INFORMATION: Part of the sequence that has been artificially
    added during the cloning process to facilitate gene expression in
    E. coli.

<400> SEQUENCE: 3

| | | | | | | |
|---|---|---|---|---|---|---|
| ttgattgatt | gaaggagaaa | tatcatggct | ctacccaagc | agatgaaact | gacataccac | 60 |
| atggagggga | ctgttaatgg | gcatttcttt | ataatcaagg | gcgaaggcgg | tggagagcct | 120 |
| tacgaaggaa | cacatactat | taagctgcaa | gtggttgaag | gaagtccact | gccattctcc | 180 |
| cctgacatat | tgtcgactgt | gtttcaatac | ggaaacaggt | gcttcactaa | atatcccccc | 240 |
| aacatagttg | actatttcaa | gaactcatgt | tctggtggcg | gatatacatt | tggaaggtct | 300 |
| tttctctatg | aagatggagc | agtttgcaca | gccagtggag | atataacatt | gagctctgat | 360 |
| aagagtagct | ttgaacacaa | atccaagttt | cttggagtca | actttcctgc | tgatggacct | 420 |
| gtgatgaaaa | aggagacgac | taattgggag | ccatcctgcg | agaaaatgac | acctaatggg | 480 |
| atgacattga | tagggatgt | cactgagttc | cttctgaaga | agatggtaa | acgttacaag | 540 |
| tgccagttcc | acacatttca | cgatgcaaag | gagaagtcga | gaaacatgcc | aatgccagac | 600 |
| ttccacttcg | tgcaacatga | gatagaaagg | aaagacctac | ccggtcctat | gcagacatgg | 660 |
| caactgacag | aacatgctgc | tgcatgtaaa | aatgtttcac | catcaccatc | acatcactaa | 720 |

<210> SEQ ID NO 4
<211> LENGTH: 733
<212> TYPE: DNA
<213> ORGANISM: Echinophyllia echinata
<220> FEATURE:
<221> NAME/KEY: misc_feature
<222> LOCATION: (1)..(24)
<223> OTHER INFORMATION: Part of the sequence that has been artificially
    added during the cloning process to facilitate gene expression in
    E. coli.
<220> FEATURE:
<221> NAME/KEY: misc_feature
<222> LOCATION: (712)..(733)
<223> OTHER INFORMATION: Part of the sequence that has been artificially
    added during the cloning process to facilitate gene expression in
    E. coli.

<400> SEQUENCE: 4

| | | | | | | |
|---|---|---|---|---|---|---|
| ttgattgatt | gaaggagaaa | tatcatgagt | gtgtttaatc | cagatatgaa | gatcaagctg | 60 |
| tatatggaag | gcgctgtaaa | cgggcacaag | ttcgagatta | aggagaagg | aaacgggaag | 120 |
| cctttttgagg | gaaaacagac | catggacctg | gcagtcgtag | acgcggacc | tctgcctttt | 180 |
| gctttcgata | tcttgacaac | ttcattcaat | tacggcaaca | gggtattcac | caaatacccca | 240 |
| gatactatag | tagactattt | caagccgtcg | tttcctgagg | ggtattcctg | ggaacgaagc | 300 |
| atgacttacg | aagatggagg | catttgcatc | gccacaaatg | acataacact | gctgaaagat | 360 |
| accgacgact | cgaactattt | ctactataaa | attcgatttg | atggtgtgaa | ctttgctgcc | 420 |
| aatggtccag | ttatgcagaa | gaagaccgcg | aaatgggagc | catccactga | gaaaatgtat | 480 |
| gtgcgtgatg | gagtgctgaa | gggtgaagtt | aacatggctc | tgttgcttga | aggaggtggc | 540 |
| cattaccgat | gtgactttaa | aactacctat | aaagctaaga | aggttgtccg | gttgccaagc | 600 |
| tatcactttg | tggaccaccg | tatagagatt | ttaagccaca | gcaaagatta | caaccaagtt | 660 |
| aggctgcatg | agcatgctga | agctcattcc | gggctgccga | gacaagccaa | gcatcaccat | 720 |
| caccatcact | aaa | | | | | 733 |

<210> SEQ ID NO 5

```
<211> LENGTH: 726
<212> TYPE: DNA
<213> ORGANISM: Mycedium elephantotus
<220> FEATURE:
<221> NAME/KEY: misc_feature
<222> LOCATION: (1)..(24)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (706)..(726)
<223> OTHER INFORMATION: Part of the sequence that has been artificially
      added during the cloning process to facilitate gene expression in
      E. coli.

<400> SEQUENCE: 5
ttgattgatt gaaggagaaa tatcatgagt gtgattaagc cagacatgag gataaggctg      60
caaatgcaag gcgcggtaaa cgggcacccg ttcgtgatta caggagaagg agagggcaag    120
ccttacgaag gaaacacac tataaacctt acagtccaag acgtggacc tctccctttc     180 gctttcgata tcttaacgac agcattccag tacggcaaca gggtattcac caaatacccca  240 aaagacatcc cagactattt caagcagtcg tttcccgcgg gtattcctg ggagcgatgc    300 atgacgttcg aagacggagg cctttgcacc gtgtcgagcc acataaaaat tgaaggtgac    360
tatttaccct acgacattcg atttcatggt gtgaactttc cagccggtgg tccagtcatg    420
cagaagaaga cgctgagatg ggagccatcc actgagaata tgtatgtgcg tgatggagtg    480
ctggtggggg aggtagagag gactctgttg cttgaaggaa ataagcatca ccgatgtaac    540
ttcagaacta cttacaaagc taagaaagaa gtggtgttac cagaatatca ctttgtggat    600
caccgaatag agatattagg ccatgacaaa gattacaaca acgtggtggt gtatgagaat    660
gcggttgccc gccagcaggc ttctactctg ccaagcaagg ccaagcatca ccatcaccat    720
cactaa                                                               726

<210> SEQ ID NO 6
<211> LENGTH: 727
<212> TYPE: DNA
<213> ORGANISM: mycedium elephantotus
<220> FEATURE:
<221> NAME/KEY: misc_feature
<222> LOCATION: (1)..(24)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (703)..(727)
<223> OTHER INFORMATION: Part of the sequence that has been artificially
      added during the cloning process to facilitate gene expression in
      E. coli.

<400> SEQUENCE: 6
ttgattgatt gaaggagaaa tatcatgaat gtgattaaac cagacatgaa gctcaagctg      60
cgcatggaag gcacggtaaa tgggcactac ttcgtgattg aaggagatgg taaaggcagg    120
ccttttgagg gaaaacagag tatggactta gatgtaaaag agggcggacc actgcctttc    180
gcctatgata tcttaacaac agcattccat tatggcaaca gggttttcgc agaatacccca   240 gatcatatac cagactattt caaacagtca tttcctggag gtattcctg ggaacgaagc     300 ctcacgtttg aagacggggg catttgcatc gccagaaacg acataaaaat ggtaggcgac    360
actttctata atacagttcg atttgatggt gttaactttc cccccaatgg tccagtgatg    420
caaaggagga cccagaaatg ggagccatcc accgagaaaa tatatgtgcg tgatggagtg    480
```

```
ttgacgggtg acattaccat ggctctgttg cttgaaggag gtgtccatta ccgatgtgac      540
ttcagaacta cttacaaagc taaggagaag ggcgtccagt tgccaggcta tcactttgta      600
gatcactgta tagaaatttt aagtcatgac aaagattata acaaggttaa actgtacgag      660
catgccgtag ctcattctgg attgccggac aacaaacggc aacatcacca tcaccatcac      720
taataaa                                                                727

<210> SEQ ID NO 7
<211> LENGTH: 768
<212> TYPE: DNA
<213> ORGANISM: Echinophyllia echinata
<220> FEATURE:
<221> NAME/KEY: misc_feature
<222> LOCATION: (1)..(24)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (697)..(712)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (713)..(768)
<223> OTHER INFORMATION: Sequence derived from the cloning vector
      pGEM-T; in this particular construct it becomes translated during
      protein expression.

<400> SEQUENCE: 7
ttgattgatt gaaggagaaa tatcatgaat gtgattaaac cagacatgaa gattaagctg      60
cgtatggaag gcgctgtaaa cgggcacaag tttgctattg aaggggaagg aaacggccag      120
cccttcgagg gaaaacagac tatgaacctg aaagtcaaag aaggtggacc tctgcctttt      180
gcttacgata tcttgacaac aatattcaat tacggcaaca gggtatttgt caaatacccca     240 gatgatatag tagactattt caagcagtcg tttcccgagg gctattcctg ggaacgcagc      300
atgatttatg aagacggagg catttgcatc gccacaaacg acataacttt ggaaggtgat      360
tgtttcgtct ataaaattcg atttgatggt gtaaacttc ccgccaaaag tccagttttg      420
cagaagatga cgaaaaaatg ggagccatcc actgagaaat tgtatgtacg tgatggagtg      480
ctgaagggtg atgttaacat ggctctgttg cttgaaggag gtggccactt ccggtgtgac      540
tttaaaacta cttacaaagc taaaaaggtt gttcaactac cagattatca ctttgtggat      600
caccgcattg aaattatgag ccacgacaaa gattacaaca acgttaagct atgtgagcat      660
gccgaagctc attccgggct gccagggcag gcgaagcatc accatcacca taatcccgcg      720
gccatggcgg ccgggagcat gcgacgtcgg gcccaattcg ccctatag                   768

<210> SEQ ID NO 8
<211> LENGTH: 736
<212> TYPE: DNA
<213> ORGANISM: Echinophyllia echinata
<220> FEATURE:
<221> NAME/KEY: misc_feature
<222> LOCATION: (1)..(30)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (709)..(709)
<223> OTHER INFORMATION: Part of the sequence that has been artificially
      added during the cloning process to facilitate gene expression in
```

E. coli.
<220> FEATURE:
<221> NAME/KEY: misc_feature
<222> LOCATION: (715)..(736)
<223> OTHER INFORMATION: Part of the sequence that has been artificially
      added during the cloning process to facilitate gene expression in
      E. coli.

<400> SEQUENCE: 8
ttagtgatga ttgattgaag gagaaatatc atgaatgtga ttaaaccaga catgaagatc       60
aggctgcgta tggaaggcgc tgtaaacggg cacaagttcg taattatcgg aaaaggagat     120
ggcaagcctt acgagggaac tcagactatg gaccttgaag tcatagaggg cggacctctg     180
ccctttgctt ttgatatctt gacaacagta ttcaaatacg caacagggc tttcgttaaa     240 tatccaacgg atatagcaga ctatttcaag caatcgtttc ctgaagggtt ttcttgggag     300
cgaagcatga cttacgaaga cggaggaatt tgcatcgcca caaatgacat aacactaagt     360
aaagacatcg ccaactgctt tgattataac attcgatttg atggtgtgaa ctttcccccg     420
aatagtccgg ttttgcagaa gacaacaata agtgggagc cttccactga aacatgtat      480 gtgcgtgatg gagttctgaa aggcgacatt aacatgtctc tgttgcttga aggaggtgca     540
ggccattacc ggtgtgactt caaaactact tacaaagcta agaaggctgt caagttgcca     600
gactatcact ttgtggacca ccgcattaca attgtaagcc acgacaagga ttacaacaaa     660
gtgaagctgc gtgagcatgc cgaagctcat tccgggctgc agatggagcc caagcatcac     720
catcaccatc actaaa                                                     736

<210> SEQ ID NO 9
<211> LENGTH: 710
<212> TYPE: DNA
<213> ORGANISM: Echinophyllia echinata
<220> FEATURE:
<221> NAME/KEY: misc_feature
<222> LOCATION: (1)..(13)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (689)..(710)
<223> OTHER INFORMATION: Part of the sequence that has been artificially
      added during the cloning process to facilitate gene expression in
      E. coli.

<400> SEQUENCE: 9
aaggagaaat atcatgagtc tgattaaacc agaaatgaag atcaagctgc ttatggaagg       60
caatgtaaac gggcacccgt ttgttattga gggagatgga aaaggccatc cttttgaggg     120
aaaacagagt atggaccttg tagtcaaaga aggcgcacct ctccctttg cctacgatat      180 cttgacaaca gcattccatt acggcaacag ggtttttgct aaatacccag accatatacc     240
agactacttc aagcagtcgt ttcccaacgg ttttcttgg gagcgaagcc tgatgttcga     300
ggacgggggc gtttgcatcg ccacaaatga cataacactg gaaggagaca cttttctttaa     360 caaagttcga ttttatggtg taaactttcc cccaaatggt cctgttatgc agaagaagac     420
gctgaaatgg gaggcatcca ctgagaaaat gtatttgcgt gatggagtgt tgacgggcga     480
tattaccatg gctctgctgc ttaaaggaga tgtccattac cgatgtgact tcagaactac     540
ttacaaatct aggcaggagg gtgtcaagtt gccaggctat cactttgtcg atcactgcat     600
cagcattgtg agccatgaca aagactacac gaaggttaag ctgtatgagc atgctgttgc     660
ccatttggga ttgccggaaa acgtcaagca tcaccatcac catcactaaa                 710

<210> SEQ ID NO 10
<211> LENGTH: 711
<212> TYPE: DNA
<213> ORGANISM: Fungia scutaria
<220> FEATURE:
<221> NAME/KEY: misc_feature
<222> LOCATION: (1)..(12)
<223> OTHER INFORMATION: Part of the sequence that has been artificially added during the cloning process to facilitate gene expression in E. coli.
<220> FEATURE:
<221> NAME/KEY: misc_feature
<222> LOCATION: (684)..(684)
<223> OTHER INFORMATION: Part of the sequence that has been artificially added during the cloning process to facilitate gene expression in E. coli.
<220> FEATURE:
<221> NAME/KEY: misc_feature
<222> LOCATION: (691)..(711)
<223> OTHER INFORMATION: Part of the sequence that has been artificially added during the cloning process to facilitate gene expression in E. coli.

<400> SEQUENCE: 10
aggagaaata tcatgagtgt gattgtaaag gaaatgatga ctaagctaca catggaaggt      60
actgttaacg ggcacgcctt tacaattgaa ggcaaaggaa aaggcgatcc ttacaatgga     120
gtgcagtcta tgaaccttga cgtcaaaggc ggtgcgcctt tgccgttctc tttcgatctt     180
ttgacgccag cattcatgta cggcaacaga gtgttcacga agtatccaga agacatacca     240 gacttttca agcaggtgtt tcctgaaggg taccactggg aaagaagtat tacctttgaa     300
gatcaggccg tttgtacggc aaccagccac ataaggctgg accagaaaga gatgtgtttt     360
atctatgacg tccgttttca cggtgtgaac tttcccgcca atgcccaat catgcagaag     420 aagatactgg gatgggagcc atccactgag aaaatgtatg cacgtgatgg ggtgctgaag     480
ggtgatgtta atatgactct tcgtgttgaa ggaggtggcc attaccgagc tgacttcagg     540
actacttaca aagcaaagaa gccagtcaac ctgccaggct atcacttcat agaccaccgc     600
attgagatta ccaagcacag caaagattac accaatgttg ctttgtatga ggcagcagtt     660
gctcgtcatt ctccgctgcc taaagttgct catcaccatc accatcacta a              711

<210> SEQ ID NO 11
<211> LENGTH: 720
<212> TYPE: DNA
<213> ORGANISM: Galaxea fascicularis
<220> FEATURE:
<221> NAME/KEY: misc_feature
<222> LOCATION: (1)..(24)
<223> OTHER INFORMATION: Part of the sequence that has been artificially added during the cloning process to facilitate gene expression in E. coli.
<220> FEATURE:
<221> NAME/KEY: misc_feature
<222> LOCATION: (700)..(720)
<223> OTHER INFORMATION: Part of the sequence that has been artificially added during the cloning process to facilitate gene expression in E. coli.

<400> SEQUENCE: 11
ttgattgatt gaaggagaaa tatcatgaat gtgattaaac cagacatgaa gatcaagctg      60
tgtatgagag gcactataaa cgggcataat ttcgtgattg aaggagaagg aaaaggaaac     120
ccttacgagg gaacgcagat tttagacctg aacgtcactg aaggcgcacc tctgccttc     180 gcttacgata tcttgacaac agtgttccag tacggcaaca gggcattcac caagtaccca     240

```
gcagatattc aggactattt caagcagact tttcctgagg ggtatcactg ggaaagaagc      300
atgacttatg aagaccaggg catttgcact gccacaagca acataagcat gcgtggcgac      360
tgttttttct atgacattcg ttttgatggt gtgaactttc ctcccaatgg tccggttatg      420
cagaagaaga ctcttaaatg ggagccatcc actgagaaaa tgtacgtacg tgatggagtg      480
ctgaagggtg atgttaacat ggctctgttg cttgaaggag gtggccatta tcgatgtgat      540
ttcaaaacta cttacaaagc aaagaaggat gtccgtttgc cagactatca ctttgtggac      600
caccgcattg agattttgaa gcatgacaaa gattacaaca aggtcgagct ctatgagaat      660
gccgttgctc gctattctat gctgccgagt caggccaagc atcaccatca ccatcactaa      720
```

<210> SEQ ID NO 12
<211> LENGTH: 699
<212> TYPE: DNA
<213> ORGANISM: Galaxea fascicularis
<220> FEATURE:
<221> NAME/KEY: misc_feature
<222> LOCATION: (1)..(14)
<223> OTHER INFORMATION: Part of the sequence that has been artificially added during the cloning process to facilitate gene expression in E. coli.
<220> FEATURE:
<221> NAME/KEY: misc_feature
<222> LOCATION: (678)..(699)
<223> OTHER INFORMATION: Part of the sequence that has been artificially added during the cloning process to facilitate gene expression in E. coli.

<400> SEQUENCE: 12

```
gaaggagaaa tatcatgagt gtgatcgcta acaaatgac ctacaaggtt tatatgtcag       60
gcacggtcaa tggacactac tttgaggtcg aaggcgatgg aaaaggaaag ccttacgagg      120
gggagcagac ggtaaagctc actgtcacca agggcggacc tctgccattt gcctgggata      180
ttttatcacc acagtctcag tacggaagca taccattcac caagtaccct gaagacatcc      240
ctgactatgt aaagcagtca tttcctgagg gatatacatg ggagaggatc atgaactttg      300
aagatggtgc agtgtgtact gtcagcaatg attccagcat ccaaggcaac tgtttcatct      360
accatgtcaa gttctctggt ttgaactttc ctcccaatgg acctgttatg cagaagaaga      420
cacagggctg ggaacccaac actgagcgtc tctttgcacg agatggaatg ctgataggaa      480
acaactttat ggctctgaag ttggaaggag gtggtcacta tttgtgtgaa ttcaaatcta      540
cttacaaggc aaagaagcct gtgaagatgc cagggtatca ctatgttgac cgcaaactgg      600
atgtaaccaa tcacaacaag gattacactt ccgttgagca gtgtgaaatt tccattgcac      660
gcaaatctgt ggtcgcccat caccatcacc atcactaaa                             699
```

<210> SEQ ID NO 13
<211> LENGTH: 744
<212> TYPE: DNA
<213> ORGANISM: Montipora efflorescens
<220> FEATURE:
<221> NAME/KEY: misc_feature
<222> LOCATION: (1)..(24)
<223> OTHER INFORMATION: Part of the sequence that has been artificially added during the cloning process to facilitate gene expression in E. coli.
<220> FEATURE:
<221> NAME/KEY: misc_feature
<222> LOCATION: (724)..(744)
<223> OTHER INFORMATION: Part of the sequence that has been artificially added during the cloning process to facilitate gene expression in E. coli.

<400> SEQUENCE: 13

```
ttgattgatt gaaggagaaa tatcatggct ctttcaaaga acggtgtcaa agacagaatg      60
aagctgaaat tccatatgga ggggagtgtc aacgggcatg aatttacaat caagggcgaa     120
ggcactgggc aaccttacga agggacacag tctattcaac tgcgtgtgga aaaagggggt     180
ccgttgccat tctccgtaga catattgtcg gctgtgtttc tgtacggaaa cagggtcttt     240
actaaatatc ctcaagacct tgttgactat ttcaagaact cgtgtcctgc tggatataca     300
tggcaaaggt ctttctctt tgaagatggt gcagtttgca cagccagtgc agatataaca      360
gtgagtgttg aggagaactg cttttatcac gagtccaagt tcatggagt gaactttcct      420 gctgatggac ctgtgatgaa aaagatgaca actaactggg aaccatcctg cgagaaaatc     480
acaccaatac ctaatgaggg gatattgaaa ggagatgtca ccatgttcct ccttctgaag     540
gatggtgggc gttaccggtg ccagttcgat acagtttaca agcaaagtc tgacccaaaa     600 acgatcatga tgccggactg gcacttcatc aacataagc tcaaccgcga agaccgcagc      660
gatgctaagc accagaaatg gcgactgta gaaaatgcta ttgcataccg atccacatta     720
tcccatcacc atcaccatca ctaa                                            744
```

<210> SEQ ID NO 14  
<211> LENGTH: 738  
<212> TYPE: DNA  
<213> ORGANISM: Porites porites  
<220> FEATURE:  
<221> NAME/KEY: misc_feature  
<222> LOCATION: (1)..(24)  
<223> OTHER INFORMATION: Part of the sequence that has been artificially added during the cloning process to facilitate gene expression in E. coli.  
<220> FEATURE:  
<221> NAME/KEY: misc_feature  
<222> LOCATION: (718)..(738)  
<223> OTHER INFORMATION: Part of the sequence that has been artificially added during the cloning process to facilitate gene expression in E. coli.

<400> SEQUENCE: 14

```
ttgattgatt gaaggagaaa tatcatggct ctttcaaagc aaagtggggt caaagatgta      60
atgaacaccg agcttcatat ggacgggatc gtcaatggac accccttga gataaaagga     120 aaaggaaagg gaaacccgta caagggtgtg cagaccatga gcttacagt cattaagggt      180 gcgcctttgc cattttctat tgacattttg ctgcctcaac acatgtatgg aagcaagcca     240
tttattaagt atcctgagag tatcccagac tacatcaagt tgtcatttcc cgagggaatc     300
acatgggaaa ggtccatgac ctttgaagat ggtgcagtgt gcactgtctc taacgactcc     360
aggctcgatg gcgactcttt catctacgaa gtcaggtttc ttggcgtgaa ctttccccga     420
gatggacctg ttatgcagaa gaagacgcga ggctgggacc cgtccacaga gagactgtat     480
gagtgtggtg ggtggcagag aggagacgtc cacatggcct tgaagttgga gaacggtggc     540
cattatacgt gcgacttcaa aactacttac aaatcaaaga agggcttgaa ggtgccaccg     600
tatcacttcg ttgaccacaa actagattta ctgagccaca acaccgatgg tgctaccttt     660
gaagagtttg aacaacgaga aattgcacat gcacatcttt ctaacttacc ggtagcccat     720
caccatcacc atcactaa                                                   738
```

<210> SEQ ID NO 15  
<211> LENGTH: 689  
<212> TYPE: DNA  
<213> ORGANISM: Porites porites  
<220> FEATURE:

-continued

```
<221> NAME/KEY: misc_feature
<222> LOCATION: (1)..(14)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (675)..(689)
<223> OTHER INFORMATION: Part of the sequence that has been artificially
      added during the cloning process to facilitate gene expression in
      E. coli.

<400> SEQUENCE: 15
taaggagaaa tatcatggct ctttcaaacc aagtgacaat gaaataccac atggatggca      60
gattcgagga caaggagttt acaatcgagg gtgaaggcac agggaagccg tacgagggga     120
agcaaaccgt gacactgtgg gtaaccaagg gtgcacccct cccattctcc tttgacatat     180
tgtcggctgt gtttctctat ggtaacagag ccttcactga ttatcctaaa ggaatcgttg     240
actatttcaa gccatctttt cctgaaggat attcatttga agaactctt gaatttgagg      300 atggcggata ttgcacagcc agtgcggata taagtcttga cagtgcaagc aactgcttca     360
tccacaagtc cagtttcaag ggcgtcaagt ttcctgacaa tggaccagtg aagcaaaaga     420
agacaactaa ctgggagccg tccatcgaga aaatgactgt gcgtgacggg atattgaagg     480
gtgatgttac catgttcctg tcgctgacag atggaggaaa tcatcgttgc cagttcagca     540
ctttatacaa agcaaagaag gctgtcaagt tgccaacgga aagccactat gtggagcacc     600
gcctggtgag gactgacctt cctaatggaa aagttcagtt ggaagagcat gctgctgcac     660
gtttaaacac cgtgcatcac catcaataa                                       689

<210> SEQ ID NO 16
<211> LENGTH: 717
<212> TYPE: DNA
<213> ORGANISM: Stylocoeniella sp
<220> FEATURE:
<221> NAME/KEY: misc_feature
<222> LOCATION: (1)..(24)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (697)..(717)
<223> OTHER INFORMATION: Part of the sequence that has been artificially
      added during the cloning process to facilitate gene expression in
      E. coli.

<400> SEQUENCE: 16
ttgattgatt gaaggagaaa tatcatggct cttacaaagc agtgtatcgc aaacgaaatg      60
acgatgactt tccacatgga tggctgcgtc aatggccatt actttactat cgaaggagaa     120
ggctccggga ggccatacga ggggaagcag atgtcaaagt ttaaagtcac caagggtggg     180 cccttccat tctcctttga catactatcg tcagcattca aatatggaaa tcgatgcttc      240
actgcgtatc ctgccggcat gcacgactac ttcaaacaag catttcctga gggaatgtca     300 tatgaagga catttacctt tgaagatgga ggagttgcta cagcgagtgg ggacataagc      360
cttaaaggta actgctttgt ccacaaatcc atgtttcacg gagtgaactt tcctgctgat     420
ggacctgtga tgaaaagaa gacaactggt tgggacccgt cctttgagaa atgactgtg      480 tgcaatggaa tattgaaggg cgatgttacc atgttcctca tgctcgaaga tggtaaaaat     540
tacaaatgcc aattccacac ttcttacaag acaaagaaac cggttacgct gccatcaaac     600
catgtcgtgg aacatcgcat tgtgaggacc aaccttgata aagctggcaa ccatgttcaa     660
```

```
ctggatgagc atgctgttgc acatgttaat cctttgcatc accatcacca tcactaa    717
```

<210> SEQ ID NO 17
<211> LENGTH: 684
<212> TYPE: DNA
<213> ORGANISM: Fungia cf danai
<220> FEATURE:
<221> NAME/KEY: misc_feature
<222> LOCATION: (664)..(684)
<223> OTHER INFORMATION: Part of the sequence that has been artificially
      added during the cloning process to facilitate gene expression in
      E. coli.

<400> SEQUENCE: 17

```
atgsctcttt caamrcaagy gattggaaaa gacatgaraa ttaactattt tatggatggc    60
agtgtgaacg ggcacgagtt tactgttaaa ggtgaaggca taggcaaacc ttacgaggga   120
caccatgaga tgacactacg cgtcactatg gctaagggcg ggccattgcc tttctcgttt   180
gacttattgt cacacacgtt ctgttatggc aatagacctt tcactaaata ccctgaagag   240
atacccgact atttcaaaca agcatttcct gaaggcctgt catgggaaag gtcattgcag   300
ttcgaagatg gtgggtttgc tgcagtcaac gcgaacataa gccttaaagg agactgcttc   360
gagcacaatt ccaaatttgt tggcgttaac tttcccgccg agggtcctgt gatgcaaaac   420
aaaagtctgg attgggagcc atctaccgag aaaattactg tctccgacgg agtgctgaag   480
ggtgatgttc cgatgttcct aaagctcgtg ggaggtggta atcataaatg ccaattcacg   540
actacttaca aagcggccaa aaaggttctt gacatgcctc aaagccattt catcttccat   600
cgcctagtca ggaaaaccga aggcaacatt accaagctgg tagaggatgt gaagctcat   660 aaccatcacc atcaccatca ctaa                                          684
```

<210> SEQ ID NO 18
<211> LENGTH: 738
<212> TYPE: DNA
<213> ORGANISM: Fungia cf danai
<220> FEATURE:
<221> NAME/KEY: misc_feature
<222> LOCATION: (1)..(24)
<223> OTHER INFORMATION: Part of the sequence that has been artificially
      added during the cloning process to facilitate gene expression in
      E. coli.
<220> FEATURE:
<221> NAME/KEY: misc_feature
<222> LOCATION: (718)..(738)
<223> OTHER INFORMATION: Part of the sequence that has been artificially
      added during the cloning process to facilitate gene expression in
      E. coli.

<400> SEQUENCE: 18

```
ttgattgatt gaaggagaaa tatcatgtct tattcaaagc agggcatcgt acaagaaatg    60
aagacgaaat accgtatgga aggcagtgtc aatggccatg aattcacgat cgaaggtgta   120
ggaactgggt acccttacga agggaaacag atgtccgaat tagtgatcat caagcctaag   180
ggaaagcccc ttccattctc ctttgacata ctgtcatcag tctttcaata tggaaacagg   240
tgcttcacaa agtaccctgc agacatgcct gactatttca agcaagcatt cccagatgga   300
atgtcatatg aaaggtcatt tctatttgag gatggagcag ttgctacagc cagctggaac   360
attcgtctcg aaggaaattg cttcatccac aattccatct tcatggcgt aaactttccc   420 gccgatggac ccgtaatgaa aaagaagaca attggctggg ataagtcctt cgaaaaaatg   480
actgtgtcta aagaggtgtt aacaggtgat gtgactatgt tcttatgct cgaaggaggt   540
```

```
ggttaccaca gatgccagtt tcactccact tacaaaacag agaagccggt cgaactgccc    600
ccgaatcatg tcgtagaaca tcaaattgtg aggaccgacc ttggccaaag tgcaaaaggc    660
ttcacagtca agctggaagc acatgctgcg gctcatgtta acctttgaa ggttcaacat    720 caccatcacc atcactaa                                                  738
```

<210> SEQ ID NO 19
<211> LENGTH: 708
<212> TYPE: DNA
<213> ORGANISM: Goniopora djiboutiensis
<220> FEATURE:
<221> NAME/KEY: misc_feature
<222> LOCATION: (1)..(24)
<223> OTHER INFORMATION: Part of the sequence that has been artificially added during the cloning process to facilitate gene expression in E. coli.
<220> FEATURE:
<221> NAME/KEY: misc_feature
<222> LOCATION: (688)..(708)
<223> OTHER INFORMATION: Part of the sequence that has been artificially added during the cloning process to facilitate gene expression in E. coli.

<400> SEQUENCE: 19

```
ttgattgatt gaaggagaaa tatcatgagt gtgatcgcta acaaatgac ctacaaggtt     60 tatatgtcag gcacggtcaa tggacactac tttgaggtcc aaggcgatgg aaaaggaaag   120
ccttacgagg gggagcagac agtaaagctg actgtcacca agggtggacc tctgccattt   180
gcttgggata ttttatcacc acaggctcag tacggaagca taccattcac caagtaccct   240
gaagacatcc ctgactatgt aaagcagtca ttccctgagg gatatacatg ggagaggatc   300
atgaactttg aagatggtgc agtgtgtact gtcagcaatg attccagcat ccaaggcaac   360
tgtttcatct acaatgtcaa gttctctggt ttgaactttc ctcccagtgg accagtcatg   420
cagaagaaga cacagggctg ggaacccaac actgagcgtc tccttgcacg agatggaatg   480
ctgataggaa acaactttat ggctctgaag ttggaaggag gtggtcacta tttgtgtgaa   540
ttcaaatcta cctacaaggc aaagaagcct gtgaagatgc cagggtatca ctttgttgac   600
cgcaaactgg atgtaaccaa tcacaaccag gattacactt ccgttgagca gtgtgaaatt   660
tccattgcac gcaaacctgt ggtcgcccat caccatcacc atcactaa                708
```

<210> SEQ ID NO 20
<211> LENGTH: 708
<212> TYPE: DNA
<213> ORGANISM: Montipora efflorescens
<220> FEATURE:
<221> NAME/KEY: misc_feature
<222> LOCATION: (1)..(24)
<223> OTHER INFORMATION: Part of the sequence that has been artificially added during the cloning process to facilitate gene expression in E. coli.
<220> FEATURE:
<221> NAME/KEY: misc_feature
<222> LOCATION: (688)..(708)
<223> OTHER INFORMATION: Part of the sequence that has been artificially added during the cloning process to facilitate gene expression in E. coli.

<400> SEQUENCE: 20

```
ttgattgatt gaaggagaaa tatcatgagt gtgatcgcta acaaatgac ctacaaggtt     60 tatatgtcag gcacggtcaa tggacactac tttgaggtcg aaggcgatgg aaaaggaaag   120
ccttacgagg gggagcagac ggtaaagctc actgtcacca agggtggacc tctgccattt   180
gcttgggata ttttatcacc actgtctcaa tacggaagca taccattcac caagtaccct   240
```

-continued

```
gaagacatcc ctgattatgt aaagcagtca ttccctgagg gatatacatg ggagaggatc      300
atgaactttg aagatggtgc agtgtgtact gtcagcaatg attccagcat ccaaggcaac      360
tgtttcatct acaatgtcaa atctctggt gtgaactttc ctcccaatgg acctgttatg       420
cagaagaaga cacagggctg ggaacccaac actgagcgtc tctttgcacg agatggaatg      480
ctgataggaa acaactttat ggctctgaag ttggaaggag gtggttacta tttgtgtgaa      540
ttcaaatcta cttacaaggc aaagaagcct gtgaggatgc agggtatca ctatgttgac       600 cgcaaactgg atgtaaccag tcacaacaag gattacacat tgttgagca gtgtgaaata      660 tccattgcac gccactcttt gctcggtcat caccatcacc atcactaa                    708
```

<210> SEQ ID NO 21
<211> LENGTH: 708
<212> TYPE: DNA
<213> ORGANISM: Stylocoeniella sp
<220> FEATURE:
<221> NAME/KEY: misc_feature
<222> LOCATION: (1)..(24)
<223> OTHER INFORMATION: Part of the sequence that has been artificially added during the cloning process to facilitate gene expression in E. coli.
<220> FEATURE:
<221> NAME/KEY: misc_feature
<222> LOCATION: (688)..(708)
<223> OTHER INFORMATION: Part of the sequence that has been artificially added during the cloning process to facilitate gene expression in E. coli.

<400> SEQUENCE: 21

```
ttgattgatt gaaggagaaa tatcatgagt gtgatcgcta acaaatgac ctacaaggtt        60 tatatgtcag gcacggtcaa tggacactac tttgaggtcc aaggcgatgg aaaaggaaag     120
ccttacgagg gggagcagac agtaaggctc actgtcacca agggtgggcc tctgccattt     180
gcatgggata ttttatcacc actgtctcag tacggaagca tacctttcac caagtacccct    240 gaagacatcc ctgattatgt aaagcagtca ttccctgagg gatatacatg ggagaggatc      300
atgaactttg aagatggtgc agtgtgtact gtcagcaayg attccagcat ccaaggcaac      360
tgtttcatct acartgtcaa atctctgggt tgaactttc ctcccaatgg acctgttatg       420
cagaagaaga cacagggctg ggaacccaac actgagcgtc tctttgcacg agatggaatg      480
ctgataggaa acaactttat ggctctgaag ttggaaggag gtggtcacta tttgtgtgaa      540
ttcaaatcta cttacaaggc aaagaagcct gtgaggatgc agggtatca ctatgttgac       600 cgcaaactgg atgtaaccag tcacaacagg gattacacat ctgttgagca gtgtgaaata     660
tccatagcac gccactcttt gctcggtcat caccatcacc atcactaa                    708
```

<210> SEQ ID NO 22
<211> LENGTH: 741
<212> TYPE: DNA
<213> ORGANISM: Montipora efflorescens
<220> FEATURE:
<221> NAME/KEY: misc_feature
<222> LOCATION: (1)..(24)
<223> OTHER INFORMATION: Part of the sequence that has been artificially added during the cloning process to facilitate gene expression in E. coli.
<220> FEATURE:
<221> NAME/KEY: misc_feature
<222> LOCATION: (721)..(741)
<223> OTHER INFORMATION: Part of the sequence that has been artificially added during the cloning process to facilitate gene expression in E. coli.

<400> SEQUENCE: 22

```
ttgattgatt gaaggagaaa tatcatggct ctttcaaagc aaagtctacc cagcgacatg    60
aaactgatat accacatgga tgggaatgtt aatgggcatt cctttgtaat caagggcgaa   120
ggcgagggaa agccttacga agggacacat actattaagc tgcaagtggt tgaaggaagt   180
ccactgccat tctccgctga catattgtcg actgtgtttc aatacggaaa caggtgcttc   240
acaaaatatc cccccaacat agttgactat ttcaagaact catgttctgg tggcggatat   300
aaatttggaa ggtcttttct ctatgaagat ggagcagttt gcacagccag tggagatata   360
acattgagcg ctgataagaa agctttgaa cacaaatcca gtttcttgg agtcaacttt     420
cctgctgatg gacctgtgat gaaaaaggag acgactaatt gggagccatc ctgcgagaaa   480
atgacaccta atgggatgac attgataggg atgtcactg ggttccttct gaaggaagat    540
ggtaaacgtt acaagtgcca gttccacaca tttcacgatg caaggataa gtcgaaaaag    600
atgccaatgc cagacttcca cttcgtgcaa cataagatag aaaggaaaga cctacccggt   660
tctatgcaga catggcgact gacagaacat gctgctgcat gtaaaacctg tttcactgag   720
catcaccatc accatcacta a                                              741
```

<210> SEQ ID NO 23
<211> LENGTH: 747
<212> TYPE: DNA
<213> ORGANISM: Montipora efflorescens
<220> FEATURE:
<221> NAME/KEY: misc_feature
<222> LOCATION: (1)..(24)
<223> OTHER INFORMATION: Part of the sequence that has been artificially added during the cloning process to facilitate gene expression in E. coli.
<220> FEATURE:
<221> NAME/KEY: misc_feature
<222> LOCATION: (727)..(747)
<223> OTHER INFORMATION: Part of the sequence that has been artificially added during the cloning process to facilitate gene expression in E. coli.

<400> SEQUENCE: 23

```
ttgattgatt gaaggagaaa tatcatggct ctttcaaaga acggtctaac aaagaacatg    60
acgacgaaat accgcatgga agggtgtgtc gatgggcata aatttgtaat cacgggcgac   120
ggcattggag atcctttcga ggggaaacag actagtattg atctgtgtgt ggttgaaggg   180
ggaccactgc cattctccga agatatattg tctgctgtgt ttgactacgg aaacagggtc   240
tttactaaat atcctcaaga ccttgttgac tatttcaaga actcgtgtcc tgctggatat   300
acatggcaaa ggtcttttct ctttgaagat ggtgcagttt gcacagccag tgcagatata   360
acagtgagtg ttgaggagaa ctgctttat cacgagtcca gtttcatgg agtgaacttt     420
cctgctgatg gacctgtgat gaaaaagatg acaactaact gggaaccatc ctgcgagaaa   480
atcacaccaa tacctaatga ggggatattg aaaggagatg tcaccatgtt cctccttctg   540
aaggatggtg ggcgttaccg gtgccagttc gatacagttt acaaagcaaa gtctgaccca   600
aaaacgatca tgatgccgga ctggcacttc atccaacata agctcaaccg cgaagaccgc   660
agcgatgcta agcaccagaa atggcgactg gtagaaaatg ctattgcata ccgatccaca   720
ttatcccatc accatcacca tcactaa                                        747
```

<210> SEQ ID NO 24
<211> LENGTH: 231
<212> TYPE: PRT
<213> ORGANISM: Montipora millepora -continued

```
<400> SEQUENCE: 24

Met Ala Leu Pro Lys Gln Met Lys Leu Thr Tyr His Met Glu Gly Thr
1               5                   10                  15

Val Asn Gly His Phe Phe Ile Ile Lys Gly Glu Gly Gly Glu Pro
            20                  25                  30

Tyr Glu Gly Thr His Thr Ile Lys Leu Gln Val Val Glu Gly Ser Pro
        35                  40                  45

Leu Pro Phe Ser Pro Asp Ile Leu Ser Thr Val Phe Gln Tyr Gly Asn
    50                  55                  60

Arg Cys Phe Thr Lys Tyr Pro Pro Asn Ile Val Asp Tyr Phe Lys Asn
65                  70                  75                  80

Ser Cys Ser Gly Gly Gly Tyr Thr Phe Gly Arg Ser Phe Leu Tyr Glu
                85                  90                  95

Asp Gly Ala Val Cys Thr Ala Ser Gly Asp Ile Thr Leu Ser Ser Asp
            100                 105                 110

Lys Ser Ser Phe Glu His Lys Ser Lys Phe Leu Gly Val Asn Phe Pro
        115                 120                 125

Ala Asp Gly Pro Val Met Lys Lys Glu Thr Thr Asn Trp Glu Pro Ser
    130                 135                 140

Cys Glu Lys Met Thr Pro Asn Gly Met Thr Leu Ile Gly Asp Val Thr
145                 150                 155                 160

Glu Phe Leu Leu Lys Lys Asp Gly Lys Arg Tyr Lys Cys Gln Phe His
                165                 170                 175

Thr Phe His Asp Ala Lys Glu Lys Ser Arg Asn Met Pro Met Pro Asp
            180                 185                 190

Phe His Phe Val Gln His Glu Ile Glu Arg Lys Asp Leu Pro Gly Pro
        195                 200                 205

Met Gln Thr Trp Gln Leu Thr Glu His Ala Ala Ala Cys Lys Asn Val
    210                 215                 220

Ser Pro Ser Pro Ser His His
225                 230

<210> SEQ ID NO 25
<211> LENGTH: 235
<212> TYPE: PRT
<213> ORGANISM: Echinophyllia echinata

<400> SEQUENCE: 25

Met Ser Val Phe Asn Pro Asp Met Lys Ile Lys Leu Tyr Met Glu Gly
1               5                   10                  15

Ala Val Asn Gly His Lys Phe Glu Ile Lys Gly Glu Gly Asn Gly Lys
            20                  25                  30

Pro Phe Glu Gly Lys Gln Thr Met Asp Leu Ala Val Val Asp Gly Gly
        35                  40                  45

Pro Leu Pro Phe Ala Phe Asp Ile Leu Thr Thr Ser Phe Asn Tyr Gly
    50                  55                  60

Asn Arg Val Phe Thr Lys Tyr Pro Asp Thr Ile Val Asp Tyr Phe Lys
65                  70                  75                  80

Pro Ser Phe Pro Glu Gly Tyr Ser Trp Glu Arg Ser Met Thr Tyr Glu
                85                  90                  95

Asp Gly Gly Ile Cys Ile Ala Thr Asn Asp Ile Thr Leu Leu Lys Asp
            100                 105                 110

Thr Asp Asp Ser Asn Tyr Phe Tyr Tyr Lys Ile Arg Phe Asp Gly Val
        115                 120                 125
```

```
Asn Phe Ala Ala Asn Gly Pro Val Met Gln Lys Lys Thr Ala Lys Trp
            130                 135                 140

Glu Pro Ser Thr Glu Lys Met Tyr Val Arg Asp Gly Val Leu Lys Gly
145                 150                 155                 160

Glu Val Asn Met Ala Leu Leu Leu Glu Gly Gly His Tyr Arg Cys
                165                 170                 175

Asp Phe Lys Thr Thr Tyr Lys Ala Lys Lys Val Val Arg Leu Pro Ser
            180                 185                 190

Tyr His Phe Val Asp His Arg Ile Glu Ile Leu Ser His Ser Lys Asp
                195                 200                 205

Tyr Asn Gln Val Arg Leu His Glu His Ala Glu Ala His Ser Gly Leu
    210                 215                 220

Pro Arg Gln Ala Lys His His His His His
225                 230                 235

<210> SEQ ID NO 26
<211> LENGTH: 233
<212> TYPE: PRT
<213> ORGANISM: Mycedium elephantotus

<400> SEQUENCE: 26

Met Ser Val Ile Lys Pro Asp Met Arg Ile Arg Leu Gln Met Gln Gly
1               5                   10                  15

Ala Val Asn Gly His Pro Phe Val Ile Thr Gly Glu Gly Glu Gly Lys
                20                  25                  30

Pro Tyr Glu Gly Lys His Thr Ile Asn Leu Thr Val Gln Asp Gly Gly
            35                  40                  45

Pro Leu Pro Phe Ala Phe Asp Ile Leu Thr Thr Ala Phe Gln Tyr Gly
50                  55                  60

Asn Arg Val Phe Thr Lys Tyr Pro Lys Asp Ile Pro Asp Tyr Phe Lys
65                  70                  75                  80

Gln Ser Phe Pro Ala Gly Tyr Ser Trp Glu Arg Cys Met Thr Phe Glu
                85                  90                  95

Asp Gly Gly Leu Cys Thr Val Ser Ser His Ile Lys Ile Glu Gly Asp
            100                 105                 110

Tyr Phe Thr Tyr Asp Ile Arg Phe His Gly Val Asn Phe Pro Ala Gly
        115                 120                 125

Gly Pro Val Met Gln Lys Lys Thr Leu Arg Trp Glu Pro Ser Thr Glu
130                 135                 140

Asn Met Tyr Val Arg Asp Gly Val Leu Val Gly Glu Val Glu Arg Thr
145                 150                 155                 160

Leu Leu Leu Glu Gly Asn Lys His His Arg Cys Asn Phe Arg Thr Thr
                165                 170                 175

Tyr Lys Ala Lys Lys Glu Val Val Leu Pro Glu Tyr His Phe Val Asp
            180                 185                 190

His Arg Ile Glu Ile Leu Gly His Asp Lys Asp Tyr Asn Asn Val Val
        195                 200                 205

Val Tyr Glu Asn Ala Val Ala Arg Gln Gln Ala Ser Thr Leu Pro Ser
    210                 215                 220

Lys Ala Lys His His His His His
225                 230

<210> SEQ ID NO 27
<211> LENGTH: 232
<212> TYPE: PRT
```

<213> ORGANISM: Mycedium elephantotus

<400> SEQUENCE: 27

```
Met Asn Val Ile Lys Pro Asp Met Lys Leu Lys Leu Arg Met Glu Gly
1               5                   10                  15

Thr Val Asn Gly His Tyr Phe Val Ile Glu Gly Asp Gly Lys Gly Arg
            20                  25                  30

Pro Phe Glu Gly Lys Gln Ser Met Asp Leu Asp Val Lys Glu Gly Gly
        35                  40                  45

Pro Leu Pro Phe Ala Tyr Asp Ile Leu Thr Thr Ala Phe His Tyr Gly
    50                  55                  60

Asn Arg Val Phe Ala Glu Tyr Pro Asp His Ile Pro Asp Tyr Phe Lys
65                  70                  75                  80

Gln Ser Phe Pro Gly Gly Tyr Ser Trp Glu Arg Ser Leu Thr Phe Glu
                85                  90                  95

Asp Gly Gly Ile Cys Ile Ala Arg Asn Asp Ile Lys Met Val Gly Asp
            100                 105                 110

Thr Phe Tyr Asn Thr Val Arg Phe Asp Gly Val Asn Phe Pro Pro Asn
        115                 120                 125

Gly Pro Val Met Gln Arg Arg Thr Gln Lys Trp Glu Pro Ser Thr Glu
    130                 135                 140

Lys Ile Tyr Val Arg Asp Gly Val Leu Thr Gly Asp Ile Thr Met Ala
145                 150                 155                 160

Leu Leu Leu Glu Gly Gly Val His Tyr Arg Cys Asp Phe Arg Thr Thr
                165                 170                 175

Tyr Lys Ala Lys Glu Lys Gly Val Gln Leu Pro Gly Tyr His Phe Val
            180                 185                 190

Asp His Cys Ile Glu Ile Leu Ser His Asp Lys Asp Tyr Asn Lys Val
        195                 200                 205

Lys Leu Tyr Glu His Ala Val Ala His Ser Gly Leu Pro Asp Asn Lys
    210                 215                 220

Arg Gln His His His His His His
225                 230
```

<210> SEQ ID NO 28
<211> LENGTH: 247
<212> TYPE: PRT
<213> ORGANISM: Echinophyllia echinata

<400> SEQUENCE: 28

```
Met Asn Val Ile Lys Pro Asp Met Lys Ile Lys Leu Arg Met Glu Gly
1               5                   10                  15

Ala Val Asn Gly His Lys Phe Ala Ile Glu Gly Glu Gly Asn Gly Gln
            20                  25                  30

Pro Phe Glu Gly Lys Gln Thr Met Asn Leu Lys Val Lys Glu Gly Gly
        35                  40                  45

Pro Leu Pro Phe Ala Tyr Asp Ile Leu Thr Thr Ile Phe Asn Tyr Gly
    50                  55                  60

Asn Arg Val Phe Val Lys Tyr Pro Asp Asp Ile Val Asp Tyr Phe Lys
65                  70                  75                  80

Gln Ser Phe Pro Glu Gly Tyr Ser Trp Glu Arg Ser Met Ile Tyr Glu
                85                  90                  95

Asp Gly Gly Ile Cys Ile Ala Thr Asn Asp Ile Thr Leu Glu Gly Asp
            100                 105                 110

Cys Phe Val Tyr Lys Ile Arg Phe Asp Gly Val Asn Phe Pro Ala Lys
```

```
            115                 120                 125
Ser Pro Val Leu Gln Lys Met Thr Lys Lys Trp Glu Pro Ser Thr Glu
    130                 135                 140

Lys Leu Tyr Val Arg Asp Gly Val Leu Lys Gly Asp Val Asn Met Ala
145                 150                 155                 160

Leu Leu Leu Glu Gly Gly His Phe Arg Cys Asp Phe Lys Thr Thr
                165                 170                 175

Tyr Lys Ala Lys Lys Val Val Gln Leu Pro Asp Tyr His Phe Val Asp
                180                 185                 190

His Arg Ile Glu Ile Met Ser His Asp Lys Asp Tyr Asn Asn Val Lys
                195                 200                 205

Leu Cys Glu His Ala Glu Ala His Ser Gly Leu Pro Gly Gln Ala Lys
    210                 215                 220

His His His His His Asn Pro Ala Ala Met Ala Ala Gly Ser Met Arg
225                 230                 235                 240

Arg Arg Ala Gln Phe Ala Leu
                245

<210> SEQ ID NO 29
<211> LENGTH: 234
<212> TYPE: PRT
<213> ORGANISM: Echinophyliia echinata

<400> SEQUENCE: 29

Met Asn Val Ile Lys Pro Asp Met Lys Ile Arg Leu Arg Met Glu Gly
1               5                   10                  15

Ala Val Asn Gly His Lys Phe Val Ile Gly Lys Gly Asp Gly Lys
                20                  25                  30

Pro Tyr Glu Gly Thr Gln Thr Met Asp Leu Glu Val Ile Glu Gly Gly
                35                  40                  45

Pro Leu Pro Phe Ala Phe Asp Ile Leu Thr Thr Val Phe Lys Tyr Gly
    50                  55                  60

Asn Arg Ala Phe Val Lys Tyr Pro Thr Asp Ile Ala Asp Tyr Phe Lys
65                  70                  75                  80

Gln Ser Phe Pro Glu Gly Phe Ser Trp Glu Arg Ser Met Thr Tyr Glu
                85                  90                  95

Asp Gly Gly Ile Cys Ile Ala Thr Asn Asp Ile Thr Leu Ser Lys Asp
                100                 105                 110

Ile Ala Asn Cys Phe Asp Tyr Asn Ile Arg Phe Asp Gly Val Asn Phe
    115                 120                 125

Pro Pro Asn Ser Pro Val Leu Gln Lys Thr Thr Ile Lys Trp Glu Pro
    130                 135                 140

Ser Thr Glu Asn Met Tyr Val Arg Asp Gly Val Leu Lys Gly Asp Ile
145                 150                 155                 160

Asn Met Ser Leu Leu Leu Glu Gly Gly Ala Gly His Tyr Arg Cys Asp
                165                 170                 175

Phe Lys Thr Thr Tyr Lys Ala Lys Lys Ala Val Lys Leu Pro Asp Tyr
                180                 185                 190

His Phe Val Asp His Arg Ile Thr Ile Val Ser His Asp Lys Asp Tyr
                195                 200                 205

Asn Lys Val Lys Leu Arg Glu His Ala Glu Ala His Ser Gly Leu Gln
    210                 215                 220

Met Glu Pro Lys His His His His His His
225                 230
```

<210> SEQ ID NO 30
<211> LENGTH: 231
<212> TYPE: PRT
<213> ORGANISM: Echinophyllia echinata

<400> SEQUENCE: 30

Met Ser Leu Ile Lys Pro Glu Met Lys Ile Lys Leu Leu Met Glu Gly
1               5                   10                  15

Asn Val Asn Gly His Pro Phe Val Ile Glu Gly Asp Gly Lys Gly His
            20                  25                  30

Pro Phe Glu Gly Lys Gln Ser Met Asp Leu Val Val Lys Glu Gly Ala
        35                  40                  45

Pro Leu Pro Phe Ala Tyr Asp Ile Leu Thr Thr Ala Phe His Tyr Gly
    50                  55                  60

Asn Arg Val Phe Ala Lys Tyr Pro Asp His Ile Pro Asp Tyr Phe Lys
65                  70                  75                  80

Gln Ser Phe Pro Asn Gly Phe Ser Trp Glu Arg Ser Leu Met Phe Glu
                85                  90                  95

Asp Gly Gly Val Cys Ile Ala Thr Asn Asp Ile Thr Leu Glu Gly Asp
            100                 105                 110

Thr Phe Phe Asn Lys Val Arg Phe Tyr Gly Val Asn Phe Pro Pro Asn
        115                 120                 125

Gly Pro Val Met Gln Lys Lys Thr Leu Lys Trp Glu Ala Ser Thr Glu
    130                 135                 140

Lys Met Tyr Leu Arg Asp Gly Val Leu Thr Gly Asp Ile Thr Met Ala
145                 150                 155                 160

Leu Leu Leu Lys Gly Asp Val His Tyr Arg Cys Asp Phe Arg Thr Thr
                165                 170                 175

Tyr Lys Ser Arg Gln Glu Gly Val Lys Leu Pro Gly Tyr His Phe Val
            180                 185                 190

Asp His Cys Ile Ser Ile Val Ser His Asp Lys Asp Tyr Thr Lys Val
        195                 200                 205

Lys Leu Tyr Glu His Ala Val Ala His Leu Gly Leu Pro Glu Asn Val
    210                 215                 220

Lys His His His His His His
225                 230

<210> SEQ ID NO 31
<211> LENGTH: 232
<212> TYPE: PRT
<213> ORGANISM: Fungia scutaria

<400> SEQUENCE: 31

Met Ser Val Ile Val Lys Glu Met Met Thr Lys Leu His Met Glu Gly
1               5                   10                  15

Thr Val Asn Gly His Ala Phe Thr Ile Glu Gly Lys Gly Lys Gly Asp
            20                  25                  30

Pro Tyr Asn Gly Val Gln Ser Met Asn Leu Asp Val Lys Gly Gly Ala
        35                  40                  45

Pro Leu Pro Phe Ser Phe Asp Leu Leu Thr Pro Ala Phe Met Tyr Gly
    50                  55                  60

Asn Arg Val Phe Thr Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95

-continued

Asp Gln Ala Val Cys Thr Ala Thr Ser His Ile Arg Leu Asp Gln Lys
                100                 105                 110

Glu Met Cys Phe Ile Tyr Asp Val Arg Phe His Gly Val Asn Phe Pro
            115                 120                 125

Ala Asn Gly Pro Ile Met Gln Lys Lys Ile Leu Gly Trp Glu Pro Ser
        130                 135                 140

Thr Glu Lys Met Tyr Ala Arg Asp Gly Val Leu Lys Gly Asp Val Asn
145                 150                 155                 160

Met Thr Leu Arg Val Glu Gly Gly His Tyr Arg Ala Asp Phe Arg
                165                 170                 175

Thr Thr Tyr Lys Ala Lys Pro Val Asn Leu Pro Gly Tyr His Phe
                180                 185                 190

Ile Asp His Arg Ile Glu Ile Thr Lys His Ser Lys Asp Tyr Thr Asn
                195                 200                 205

Val Ala Leu Tyr Glu Ala Ala Val Ala Arg His Ser Pro Leu Pro Lys
        210                 215                 220

Val Ala His His His His His His
225                 230

<210> SEQ ID NO 32
<211> LENGTH: 231
<212> TYPE: PRT
<213> ORGANISM: Galaxea fascicularis

<400> SEQUENCE: 32

Met Asn Val Ile Lys Pro Asp Met Lys Ile Lys Leu Cys Met Arg Gly
1               5                   10                  15

Thr Ile Asn Gly His Asn Phe Val Ile Glu Gly Glu Gly Lys Gly Asn
                20                  25                  30

Pro Tyr Glu Gly Thr Gln Ile Leu Asp Leu Asn Val Thr Glu Gly Ala
            35                  40                  45

Pro Leu Pro Phe Ala Tyr Asp Ile Leu Thr Thr Val Phe Gln Tyr Gly
        50                  55                  60

Asn Arg Ala Phe Thr Lys Tyr Pro Ala Asp Ile Gln Asp Tyr Phe Lys
65                  70                  75                  80

Gln Thr Phe Pro Glu Gly Tyr His Trp Glu Arg Ser Met Thr Tyr Glu
                85                  90                  95

Asp Gln Gly Ile Cys Thr Ala Thr Ser Asn Ile Ser Met Arg Gly Asp
                100                 105                 110

Cys Phe Phe Tyr Asp Ile Arg Phe Asp Gly Val Asn Phe Pro Pro Asn
            115                 120                 125

Gly Pro Val Met Gln Lys Lys Thr Leu Lys Trp Glu Pro Ser Thr Glu
        130                 135                 140

Lys Met Tyr Val Arg Asp Gly Val Leu Lys Gly Asp Val Asn Met Ala
145                 150                 155                 160

Leu Leu Leu Glu Gly Gly His Tyr Arg Cys Asp Phe Lys Thr Thr
                165                 170                 175

Tyr Lys Ala Lys Lys Asp Val Arg Leu Pro Asp Tyr His Phe Val Asp
            180                 185                 190

His Arg Ile Glu Ile Leu Lys His Asp Lys Asp Tyr Asn Lys Val Glu
        195                 200                 205

Leu Tyr Glu Asn Ala Val Ala Arg Tyr Ser Met Leu Pro Ser Gln Ala
        210                 215                 220

Lys His His His His His His
225                 230

-continued

<210> SEQ ID NO 33
<211> LENGTH: 227
<212> TYPE: PRT
<213> ORGANISM: Galaxea fascicularis

<400> SEQUENCE: 33

Met Ser Val Ile Ala Lys Gln Met Thr Tyr Lys Val Tyr Met Ser Gly
1               5                   10                  15

Thr Val Asn Gly His Tyr Phe Glu Val Glu Gly Asp Gly Lys Gly Lys
            20                  25                  30

Pro Tyr Glu Gly Glu Gln Thr Val Lys Leu Thr Val Thr Lys Gly Gly
        35                  40                  45

Pro Leu Pro Phe Ala Trp Asp Ile Leu Ser Pro Gln Ser Gln Tyr Gly
    50                  55                  60

Ser Ile Pro Phe Thr Lys Tyr Pro Glu Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr His Val Lys Phe Ser Gly Leu Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Met Leu Ile Gly Asn Asn Phe Met Ala
145                 150                 155                 160

Leu Lys Leu Glu Gly Gly His Tyr Leu Cys Glu Phe Lys Ser Thr
                165                 170                 175

Tyr Lys Ala Lys Lys Pro Val Lys Met Pro Gly Tyr His Tyr Val Asp
            180                 185                 190

Arg Lys Leu Asp Val Thr Asn His Asn Lys Asp Tyr Thr Ser Val Glu
        195                 200                 205

Gln Cys Glu Ile Ser Ile Ala Arg Lys Ser Val Val Ala His His His
    210                 215                 220

His His His
225

<210> SEQ ID NO 34
<211> LENGTH: 239
<212> TYPE: PRT
<213> ORGANISM: Montipora efflorescens

<400> SEQUENCE: 34

Met Ala Leu Ser Lys Asn Gly Val Lys Asp Arg Met Lys Leu Lys Phe
1               5                   10                  15

His Met Glu Gly Ser Val Asn Gly His Glu Phe Thr Ile Lys Gly Glu
            20                  25                  30

Gly Thr Gly Gln Pro Tyr Glu Gly Thr Gln Ser Ile Gln Leu Arg Val
        35                  40                  45

Glu Lys Gly Gly Pro Leu Pro Phe Ser Val Asp Ile Leu Ser Ala Val
    50                  55                  60

Phe Leu Tyr Gly Asn Arg Val Phe Thr Lys Tyr Pro Gln Asp Leu Val
65                  70                  75                  80

Asp Tyr Phe Lys Asn Ser Cys Pro Ala Gly Tyr Thr Trp Gln Arg Ser
                85                  90                  95

```
Phe Leu Phe Glu Asp Gly Ala Val Cys Thr Ala Ser Ala Asp Ile Thr
                100                 105                 110
Val Ser Val Glu Glu Asn Cys Phe Tyr His Glu Ser Lys Phe His Gly
            115                 120                 125
Val Asn Phe Pro Ala Asp Gly Pro Val Met Lys Lys Met Thr Thr Asn
        130                 135                 140
Trp Glu Pro Ser Cys Glu Lys Ile Thr Pro Ile Pro Asn Glu Gly Ile
145                 150                 155                 160
Leu Lys Gly Asp Val Thr Met Phe Leu Leu Lys Asp Gly Gly Arg
                165                 170                 175
Tyr Arg Cys Gln Phe Asp Thr Val Tyr Lys Ala Lys Ser Asp Pro Lys
                180                 185                 190
Thr Ile Met Met Pro Asp Trp His Phe Ile Gln His Lys Leu Asn Arg
            195                 200                 205
Glu Asp Arg Ser Asp Ala Lys His Gln Lys Trp Arg Leu Val Glu Asn
        210                 215                 220
Ala Ile Ala Tyr Arg Ser Thr Leu Ser His His His His His
225                 230                 235

<210> SEQ ID NO 35
<211> LENGTH: 237
<212> TYPE: PRT
<213> ORGANISM: Porites porites

<400> SEQUENCE: 35

Met Ala Leu Ser Lys Gln Ser Gly Val Lys Asp Val Met Asn Thr Glu
1               5                   10                  15
Leu His Met Asp Gly Ile Val Asn Gly His Pro Phe Glu Ile Lys Gly
            20                  25                  30
Lys Gly Lys Gly Asn Pro Tyr Lys Gly Val Gln Thr Met Lys Leu Thr
        35                  40                  45
Val Ile Lys Gly Ala Pro Leu Pro Phe Ser Ile Asp Ile Leu Leu Pro
    50                  55                  60
Gln His Met Tyr Gly Ser Lys Pro Phe Ile Lys Tyr Pro Glu Ser Ile
65                  70                  75                  80
Pro Asp Tyr Ile Lys Leu Ser Phe Pro Glu Gly Ile Thr Trp Glu Arg
                85                  90                  95
Ser Met Thr Phe Glu Asp Gly Ala Val Cys Thr Val Ser Asn Asp Ser
                100                 105                 110
Arg Leu Asp Gly Asp Ser Phe Ile Tyr Glu Val Arg Phe Leu Gly Val
            115                 120                 125
Asn Phe Pro Arg Asp Gly Pro Val Met Gln Lys Lys Thr Arg Gly Trp
        130                 135                 140
Asp Pro Ser Thr Glu Arg Leu Tyr Glu Cys Gly Gly Trp Gln Arg Gly
145                 150                 155                 160
Asp Val His Met Ala Leu Lys Leu Glu Asn Gly Gly His Tyr Thr Cys
                165                 170                 175
Asp Phe Lys Thr Thr Tyr Lys Ser Lys Gly Leu Lys Val Pro Pro
                180                 185                 190
Tyr His Phe Val Asp His Lys Leu Asp Leu Leu Ser His Asn Thr Asp
            195                 200                 205
Gly Ala Thr Phe Glu Glu Phe Glu Gln Arg Glu Ile Ala His Ala His
        210                 215                 220
Leu Ser Asn Leu Pro Val Ala His His His His His
```

-continued

```
       225             230             235

<210> SEQ ID NO 36
<211> LENGTH: 224
<212> TYPE: PRT
<213> ORGANISM: Porites porites

<400> SEQUENCE: 36

Met Ala Leu Ser Asn Gln Val Thr Met Lys Tyr His Met Asp Gly Arg
1               5                   10                  15

Phe Glu Asp Lys Glu Phe Thr Ile Glu Gly Glu Gly Thr Gly Lys Pro
            20                  25                  30

Tyr Glu Gly Lys Gln Thr Val Thr Leu Trp Val Thr Lys Gly Ala Pro
        35                  40                  45

Leu Pro Phe Ser Phe Asp Ile Leu Ser Ala Val Phe Leu Tyr Gly Asn
    50                  55                  60

Arg Ala Phe Thr Asp Tyr Pro Lys Gly Ile Val Asp Tyr Phe Lys Pro
65                  70                  75                  80

Ser Phe Pro Glu Gly Tyr Ser Phe Glu Arg Thr Leu Glu Phe Glu Asp
                85                  90                  95

Gly Gly Tyr Cys Thr Ala Ser Ala Asp Ile Ser Leu Asp Ser Ala Ser
            100                 105                 110

Asn Cys Phe Ile His Lys Ser Phe Lys Gly Val Lys Phe Pro Asp
        115                 120                 125

Asn Gly Pro Val Lys Gln Lys Lys Thr Thr Asn Trp Glu Pro Ser Ile
    130                 135                 140

Glu Lys Met Thr Val Arg Asp Gly Ile Leu Lys Gly Asp Val Thr Met
145                 150                 155                 160

Phe Leu Ser Leu Thr Asp Gly Gly Asn His Arg Cys Gln Phe Ser Thr
                165                 170                 175

Leu Tyr Lys Ala Lys Lys Ala Val Lys Leu Pro Thr Glu Ser His Tyr
            180                 185                 190

Val Glu His Arg Leu Val Arg Thr Asp Leu Pro Asn Gly Lys Val Gln
        195                 200                 205

Leu Glu Glu His Ala Ala Ala Arg Leu Asn Thr Val His His Gln
    210                 215                 220

<210> SEQ ID NO 37
<211> LENGTH: 230
<212> TYPE: PRT
<213> ORGANISM: Stylocoeniella sp

<400> SEQUENCE: 37

Met Ala Leu Thr Lys Gln Cys Ile Ala Asn Glu Met Thr Met Thr Phe
1               5                   10                  15

His Met Asp Gly Cys Val Asn Gly His Tyr Phe Thr Ile Glu Gly Glu
            20                  25                  30

Gly Ser Gly Arg Pro Tyr Glu Gly Lys Gln Met Ser Lys Phe Lys Val
        35                  40                  45

Thr Lys Gly Gly Pro Leu Pro Phe Ser Phe Asp Ile Leu Ser Ser Ala
    50                  55                  60

Phe Lys Tyr Gly Asn Arg Cys Phe Thr Ala Tyr Pro Ala Gly Met His
65                  70                  75                  80

Asp Tyr Phe Lys Gln Ala Phe Pro Glu Gly Met Ser Tyr Glu Arg Thr
                85                  90                  95

Phe Thr Phe Glu Asp Gly Gly Val Ala Thr Ala Ser Gly Asp Ile Ser
```

```
                    100                 105                 110
Leu Lys Gly Asn Cys Phe Val His Lys Ser Met Phe His Gly Val Asn
            115                 120                 125

Phe Pro Ala Asp Gly Pro Val Met Lys Lys Thr Thr Gly Trp Asp
    130                 135                 140

Pro Ser Phe Glu Lys Met Thr Val Cys Asn Gly Ile Leu Lys Gly Asp
145                 150                 155                 160

Val Thr Met Phe Leu Met Leu Glu Asp Gly Lys Asn Tyr Lys Cys Gln
                165                 170                 175

Phe His Thr Ser Tyr Lys Thr Lys Pro Val Thr Leu Pro Ser Asn
            180                 185                 190

His Val Val Glu His Arg Ile Val Arg Thr Asn Leu Asp Lys Ala Gly
            195                 200                 205

Asn His Val Gln Leu Asp Glu His Ala Val Ala His Val Asn Pro Leu
    210                 215                 220

His His His His His His
225                 230

<210> SEQ ID NO 38
<211> LENGTH: 227
<212> TYPE: PRT
<213> ORGANISM: Fungia cf danai
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 38

Met Xaa Leu Ser Xaa Gln Xaa Ile Gly Lys Asp Met Xaa Ile Asn Tyr
1               5                   10                  15

Phe Met Asp Gly Ser Val Asn Gly His Glu Phe Thr Val Lys Gly Glu
            20                  25                  30

Gly Ile Gly Lys Pro Tyr Glu Gly His His Glu Met Thr Leu Arg Val
        35                  40                  45

Thr Met Ala Lys Gly Gly Pro Leu Pro Phe Ser Phe Asp Leu Leu Ser
    50                  55                  60

His Thr Phe Cys Tyr Gly Asn Arg Pro Phe Thr Lys Tyr Pro Glu Glu
65                  70                  75                  80

Ile Pro Asp Tyr Phe Lys Gln Ala Phe Pro Glu Gly Leu Ser Trp Glu
                85                  90                  95

Arg Ser Leu Gln Phe Glu Asp Gly Gly Phe Ala Ala Val Asn Ala Asn
            100                 105                 110

Ile Ser Leu Lys Gly Asp Cys Phe Glu His Asn Ser Lys Phe Val Gly
            115                 120                 125

Val Asn Phe Pro Ala Glu Gly Pro Val Met Gln Asn Lys Ser Leu Asp
    130                 135                 140

Trp Glu Pro Ser Thr Glu Lys Ile Thr Val Ser Asp Gly Val Leu Lys
145                 150                 155                 160
```

```
Gly Asp Val Pro Met Phe Leu Lys Leu Val Gly Gly Asn His Lys
            165                 170                 175

Cys Gln Phe Thr Thr Thr Tyr Lys Ala Ala Lys Lys Val Leu Asp Met
                180                 185                 190

Pro Gln Ser His Phe Ile Phe His Arg Leu Val Arg Lys Thr Glu Gly
            195                 200                 205

Asn Ile Thr Lys Leu Val Glu Asp Val Glu Ala His Asn His His His
        210                 215                 220

His His His
225
```

<210> SEQ ID NO 39
<211> LENGTH: 237
<212> TYPE: PRT
<213> ORGANISM: Fungia cf danai

<400> SEQUENCE: 39

```
Met Ser Tyr Ser Lys Gln Gly Ile Val Gln Glu Met Lys Thr Lys Tyr
1               5                   10                  15

Arg Met Glu Gly Ser Val Asn Gly His Glu Phe Thr Ile Glu Gly Val
                20                  25                  30

Gly Thr Gly Tyr Pro Tyr Glu Gly Lys Gln Met Ser Glu Leu Val Ile
            35                  40                  45

Ile Lys Pro Lys Gly Lys Pro Leu Pro Phe Ser Phe Asp Ile Leu Ser
        50                  55                  60

Ser Val Phe Gln Tyr Gly Asn Arg Cys Phe Thr Lys Tyr Pro Ala Asp
65                  70                  75                  80

Met Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Asn
            100                 105                 110

Ile Arg Leu Glu Gly Asn Cys Phe Ile His Asn Ser Ile Phe His Gly
        115                 120                 125

Val Asn Phe Pro Ala Asp Gly Pro Val Met Lys Lys Lys Thr Ile Gly
    130                 135                 140

Trp Asp Lys Ser Phe Glu Lys Met Thr Val Ser Lys Glu Val Leu Thr
145                 150                 155                 160

Gly Asp Val Thr Met Phe Leu Met Leu Glu Gly Gly Tyr His Arg
                165                 170                 175

Cys Gln Phe His Ser Thr Tyr Lys Thr Glu Lys Pro Val Glu Leu Pro
                180                 185                 190

Pro Asn His Val Val Glu His Gln Ile Val Arg Thr Asp Leu Gly Gln
            195                 200                 205

Ser Ala Lys Gly Phe Thr Val Lys Leu Glu Ala His Ala Ala Ala His
        210                 215                 220

Val Asn Pro Leu Lys Val Gln His His His His His
225                 230                 235
```

<210> SEQ ID NO 40
<211> LENGTH: 227
<212> TYPE: PRT
<213> ORGANISM: Goniopora djiboutiensis

<400> SEQUENCE: 40

```
Met Ser Val Ile Ala Lys Gln Met Thr Tyr Lys Val Tyr Met Ser Gly
1               5                   10                  15
```

-continued

```
Thr Val Asn Gly His Tyr Phe Glu Val Gln Gly Asp Gly Lys Gly Lys
             20                  25                  30
Pro Tyr Glu Gly Glu Gln Thr Val Lys Leu Thr Val Thr Lys Gly Gly
             35                  40                  45
Pro Leu Pro Phe Ala Trp Asp Ile Leu Ser Pro Gln Ala Gln Tyr Gly
 50                  55                  60
Ser Ile Pro Phe Thr Lys Tyr Pro Glu Asp Ile Pro Asp Tyr Val Lys
 65                  70                  75                  80
Gln Ser Phe Pro Glu Gly Tyr Thr Trp Glu Arg Ile Met Asn Phe Glu
                     85                  90                  95
Asp Gly Ala Val Cys Thr Val Ser Asn Asp Ser Ser Ile Gln Gly Asn
                 100                 105                 110
Cys Phe Ile Tyr Asn Val Lys Phe Ser Gly Leu Asn Phe Pro Pro Ser
                 115                 120                 125
Gly Pro Val Met Gln Lys Lys Thr Gln Gly Trp Glu Pro Asn Thr Glu
 130                 135                 140
Arg Leu Leu Ala Arg Asp Gly Met Leu Ile Gly Asn Asn Phe Met Ala
 145                 150                 155                 160
Leu Lys Leu Glu Gly Gly Gly His Tyr Leu Cys Glu Phe Lys Ser Thr
                     165                 170                 175
Tyr Lys Ala Lys Lys Pro Val Lys Met Pro Gly Tyr His Phe Val Asp
                 180                 185                 190
Arg Lys Leu Asp Val Thr Asn His Asn Gln Asp Tyr Thr Ser Val Glu
                 195                 200                 205
Gln Cys Glu Ile Ser Ile Ala Arg Lys Pro Val Val Ala His His His
                 210                 215                 220
His His His
225

<210> SEQ ID NO 41
<211> LENGTH: 227
<212> TYPE: PRT
<213> ORGANISM: Montipora efflorescens

<400> SEQUENCE: 41

Met Ser Val Ile Ala Lys Gln Met Thr Tyr Lys Val Tyr Met Ser Gly
 1                5                  10                  15
Thr Val Asn Gly His Tyr Phe Glu Val Glu Gly Asp Gly Lys Gly Lys
             20                  25                  30
Pro Tyr Glu Gly Glu Gln Thr Val Lys Leu Thr Val Thr Lys Gly Gly
             35                  40                  45
Pro Leu Pro Phe Ala Trp Asp Ile Leu Ser Pro Leu Gln Tyr Gly
 50                  55                  60
Ser Ile Pro Phe Thr Lys Tyr Pro Glu Asp Ile Pro Asp Tyr Val Lys
 65                  70                  75                  80
Gln Ser Phe Pro Glu Gly Tyr Thr Trp Glu Arg Ile Met Asn Phe Glu
                     85                  90                  95
Asp Gly Ala Val Cys Thr Val Ser Asn Asp Ser Ser Ile Gln Gly Asn
                 100                 105                 110
Cys Phe Ile Tyr Asn Val Lys Ile Ser Gly Val Asn Phe Pro Pro Asn
                 115                 120                 125
Gly Pro Val Met Gln Lys Lys Thr Gln Gly Trp Glu Pro Asn Thr Glu
 130                 135                 140
Arg Leu Phe Ala Arg Asp Gly Met Leu Ile Gly Asn Asn Phe Met Ala
```

-continued

```
                145                 150                 155                 160
Leu Lys Leu Glu Gly Gly Gly Tyr Tyr Leu Cys Glu Phe Lys Ser Thr
                    165                 170                 175

Tyr Lys Ala Lys Lys Pro Val Arg Met Pro Gly Tyr His Tyr Val Asp
                180                 185                 190

Arg Lys Leu Asp Val Thr Ser His Asn Lys Asp Tyr Thr Phe Val Glu
            195                 200                 205

Gln Cys Glu Ile Ser Ile Ala Arg His Ser Leu Leu Gly His His His
        210                 215                 220

His His His
225

<210> SEQ ID NO 42
<211> LENGTH: 227
<212> TYPE: PRT
<213> ORGANISM: Stylocoeniella

<400> SEQUENCE: 42

Met Ser Val Ile Ala Lys Gln Met Thr Tyr Lys Val Tyr Met Ser Gly
1               5                   10                  15

Thr Val Asn Gly His Tyr Phe Glu Val Gln Gly Asp Gly Lys Gly Lys
                20                  25                  30

Pro Tyr Glu Gly Glu Gln Thr Val Arg Leu Thr Val Thr Lys Gly Gly
            35                  40                  45

Pro Leu Pro Phe Ala Trp Asp Ile Leu Ser Pro Leu Ser Gln Tyr Gly
        50                  55                  60

Ser Ile Pro Phe Thr Lys Tyr Pro Glu Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr Asn Val Lys Ile Ser Gly Leu Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Met Leu Ile Gly Asn Asn Phe Met Ala
145                 150                 155                 160

Leu Lys Leu Glu Gly Gly Gly His Tyr Leu Cys Glu Phe Lys Ser Thr
                    165                 170                 175

Tyr Lys Ala Lys Lys Pro Val Arg Met Pro Gly Tyr His Tyr Val Asp
                180                 185                 190

Arg Lys Leu Asp Val Thr Ser His Asn Arg Asp Tyr Thr Ser Val Glu
            195                 200                 205

Gln Cys Glu Ile Ser Ile Ala Arg His Ser Leu Leu Gly His His His
        210                 215                 220

His His His
225

<210> SEQ ID NO 43
<211> LENGTH: 238
<212> TYPE: PRT
<213> ORGANISM: Montipora efflorescens

<400> SEQUENCE: 43

Met Ala Leu Ser Lys Gln Ser Leu Pro Ser Asp Met Lys Leu Ile Tyr
```

```
            1               5                  10                 15
          His Met Asp Gly Asn Val Asn Gly His Ser Phe Val Ile Lys Gly Glu
                         20                  25                 30

Gly Glu Gly Lys Pro Tyr Glu Gly Thr His Thr Ile Lys Leu Gln Val
                         35                  40              45

Val Glu Gly Ser Pro Leu Pro Phe Ser Ala Asp Ile Leu Ser Thr Val
                     50                  55                  60

Phe Gln Tyr Gly Asn Arg Cys Phe Thr Lys Tyr Pro Asn Ile Val
           65                  70                  75                  80

Asp Tyr Phe Lys Asn Ser Cys Ser Gly Gly Tyr Lys Phe Gly Arg
                              85                  90                  95

Ser Phe Leu Tyr Glu Asp Gly Ala Val Cys Thr Ala Ser Gly Asp Ile
                         100                 105                 110

Thr Leu Ser Ala Asp Lys Lys Ser Phe Glu His Lys Ser Lys Phe Leu
                         115                 120                 125

Gly Val Asn Phe Pro Ala Asp Gly Pro Val Met Lys Lys Glu Thr Thr
                         130                 135                 140

Asn Trp Glu Pro Ser Cys Glu Lys Met Thr Pro Asn Gly Met Thr Leu
          145                 150                 155                 160

Ile Gly Asp Val Thr Gly Phe Leu Leu Lys Glu Asp Gly Lys Arg Tyr
                              165                 170                 175

Lys Cys Gln Phe His Thr Phe His Asp Ala Lys Asp Lys Ser Lys Lys
                         180                 185                 190

Met Pro Met Pro Asp Phe His Phe Val Gln His Lys Ile Glu Arg Lys
                         195                 200                 205

Asp Leu Pro Gly Ser Met Gln Thr Trp Arg Leu Thr Glu His Ala Ala
                         210                 215                 220

Ala Cys Lys Thr Cys Phe Thr Glu His His His His His
          225                 230                 235

<210> SEQ ID NO 44
<211> LENGTH: 240
<212> TYPE: PRT
<213> ORGANISM: Montipora efflorescens

<400> SEQUENCE: 44

Met Ala Leu Ser Lys Asn Gly Leu Thr Lys Asn Met Thr Thr Lys Tyr
 1               5                  10                  15

Arg Met Glu Gly Cys Val Asp Gly His Lys Phe Val Ile Thr Gly Asp
                20                  25                  30

Gly Ile Gly Asp Pro Phe Glu Gly Lys Gln Thr Ser Ile Asp Leu Cys
            35                  40                  45

Val Val Glu Gly Gly Pro Leu Pro Phe Ser Glu Asp Ile Leu Ser Ala
        50                  55                  60

Val Phe Asp Tyr Gly Asn Arg Val Phe Thr Lys Tyr Pro Gln Asp Leu
 65                  70                  75                  80

Val Asp Tyr Phe Lys Asn Ser Cys Pro Ala Gly Tyr Thr Trp Gln Arg
                85                  90                  95

Ser Phe Leu Phe Glu Asp Gly Ala Val Cys Thr Ala Ser Ala Asp Ile
            100                 105                 110

Thr Val Ser Val Glu Glu Asn Cys Phe Tyr His Glu Ser Lys Phe His
        115                 120                 125

Gly Val Asn Phe Pro Ala Asp Gly Pro Val Met Lys Lys Met Thr Thr
            130                 135                 140
```

-continued

```
Asn Trp Glu Pro Ser Cys Glu Lys Ile Thr Pro Ile Pro Asn Glu Gly
145                 150                 155                 160

Ile Leu Lys Gly Asp Val Thr Met Phe Leu Leu Lys Asp Gly Gly
                165                 170                 175

Arg Tyr Arg Cys Gln Phe Asp Thr Val Tyr Lys Ala Lys Ser Asp Pro
            180                 185                 190

Lys Thr Ile Met Met Pro Asp Trp His Phe Ile Gln His Lys Leu Asn
        195                 200                 205

Arg Glu Asp Arg Ser Asp Ala Lys His Gln Lys Trp Arg Leu Val Glu
    210                 215                 220

Asn Ala Ile Ala Tyr Arg Ser Thr Leu Ser His His His His His His
225                 230                 235                 240
```

FLUORESCENT AND COLORED PROTEINS, AND POLYNUCLEOTIDES THAT ENCODE THESE PROTEINS

GOVERNMENT SUPPORT

The subject matter of this application has been supported in part by U.S. Government Support under NIH RO1 GM066243-01. Accordingly, the U.S. Government has certain rights in this invention.

FIELD OF THE INVENTION

The present invention relates to novel fluorescent and colored proteins, and their use. These materials and methods are particularly advantageous for labeling and detection technology. Specifically, exemplified are novel colored and/or fluorescent proteins, and mutants thereof, isolated from marine organisms. These new proteins offer a wider array of colors and biochemical features compared to existing wild-type green fluorescent protein (GFP) or its modified variants utilized in current labeling and detection technology.

BACKGROUND OF THE INVENTION

Genetic markers are important for monitoring gene expression and tracking movement of proteins in cells. Markers have been extensively used for monitoring biological activity of genetic elements such as promoters, enhancers and terminators, and other aspects of gene regulation in numerous biological systems. Over the years numerous marker genes have been developed and utilized widely in molecular and genetic studies aimed at the identification, isolation and characterization of genetic regulatory elements and genes, and the development of gene transfer techniques.

In general, markers can be grouped into selectable markers and reporter markers. Selectable markers are typically enzymes with catalytic capability to convert chemical substrates usually harmful to host cells into non-toxic products, thus providing transformed host cells a conditionally selectable growth advantage under selective environment and allowing the recovery of stable transformants after transformation. A number of commonly used selectable markers include those that confer resistance characteristics to antibiotics (Gritz and Davies 1983; Bevan et al., 1983) and herbicides (De Block et al., 1987), and those with enzymatic activity to detoxify metabolic compounds that can adversely affect cell growth (Joersbo and Okkels 1996).

Reporter markers are compounds that provide biochemically assayable or identifiable activities. Reporter markers have been widely used in studies to reveal biological functions and modes of action of genetic elements such as promoters, enhancers, terminators, and regulatory proteins including signal peptides, transcription factors and related gene products. Over the years, several reporter markers have been developed for use in both prokaryotic and eukaryotic systems, including β-galactosidase (LacZ) (Stanley and Luzio 1984), β-glucuronidase (GUS) (Jefferson et al., 1987; U.S. Pat. No. 5,268,463), chloramphenicol acetyltransferase (CAT) (Gorman et al., 1982), green fluorescent protein (GFP) (Prasher et al., 1992; U.S. Pat. No. 5,491,084) and luciferase (Luc) (Ow et al., 1986).

Among reporter markers, GUS offers a sensitive and versatile reporting capability for gene expression in plants. β-glucuronidase or GUS, encoded by the uidA gene from *Escherichia coli*, catalyzes the conversion of several colorigenic and fluorogenic glucorogenic substrates such as p-nitrophenyl β-D-glucuronide and 4-methylumbelliferyl β-D-glucuronide into easily detectable products. GUS activity can be measured by highly sensitive colorimetric and fluorimetric methods (Jefferson et al., 1987). However, the GUS assay often requires total destruction of the sample tissues or exposure of sample tissues to phytotoxic chemical substrates. This prevents repeated use of the same sample tissue for continuous expression analysis and precludes the recovery of transformants from analyzed materials.

Recently, GFP isolated from the Pacific Northwest jellyfish (*Aequorea victoria*) has become an important reporter marker for non-destructive analysis of gene expression. GFP fluoresces in vivo by receiving light energy without the involvement of any chemical substrates. Thus, GFP is especially suitable for real time and continuous monitoring of temporal and spatial control of gene expression and protein activities without any physical damage to assay samples.

The gene for GFP has been cloned and used as a reporter gene, which can be expressed as a functional transgene in living organisms, marking the organisms with fluorescent color and thus allowing detection of those organisms. Accordingly, GFP has become a versatile fluorescent marker for monitoring a variety of physiological processes, visualizing protein localization and detecting the expression of transferred genes in various living systems, including bacteria, fungi, and mammalian tissues.

This in vivo labeling and detection technology was originally based on a single fluorescent protein: the green fluorescent protein from *Aequorea victoria*. Numerous modifications have been made to alter the spectral properties of GFP to provide for significant enhancement in fluorescence intensity (Prasher et al., 1992; Cubitt et al., 1995, Heim et al., 1994, 1995; Cormack et al., 1996; U.S. Pat. No. 5,804, 387). In addition, GFP genes have been modified to contain more silent base mutations that correspond to codon-usage preferences in order to improve its expression efficacy, making it a reporter gene in both animal and plant systems (U.S. Pat. Nos. 5,874,304; 5,968,750; and 6,020,192).

In addition to GFP, there are now a number of other fluorescent proteins, substantially different from GFP, which are being developed into biotechnology tools. Most prominent of these proteins is the red fluorescent protein DsRed. See, for example, Labas, Y. A., N. G. Gurskaya, Y. G. Yanushevich, A. F. Fradkov, K. A. Lukyanov, S. A. Lukyanov and M. V. Matz. (2002) "Diversity and evolution of the green fluorescent protein family" *Proc Natl Acad Sci USA* 99:4256–4261 and Matz, M. V., K. A. Lukyanov and S. A. Lukyanov (2002) "Family of the green fluorescent protein: journey to the end of the rainbow" *Bioessays* 24: 953–959.

Labeling technologies based on GFP and related proteins have become indispensable in such areas as basic biomedical research, cell and molecular biology, transgenic research and drug discovery. The number of PubMed records containing the phrase "green fluorescent protein" exceeds 5500 only within the last three years. Demand for labeling and detection based on the fluorescent protein technology is large and steady.

Currently, there are very few known natural pigments essentially encoded by a single gene, wherein both the substrate for pigment biosynthesis and the necessary catalytic moieties are provided within a single polypeptide chain. The limited availability of fluorescent marker proteins makes the current technology based on fluorescent proteins very expensive, rendering it unaffordable and inaccessible to many mid-size (or smaller) companies that are interested in using the technology. Therefore, there is a need for less expensive, readily available fluorescent and/or colored materials.

BRIEF SUMMARY OF THE INVENTION

The subject invention provides new fluorescent and/or colored proteins, and polynucleotide sequences that encode these proteins. The subject invention further provides materials and methods useful for expressing these detectable proteins in biological systems.

In specific embodiments, the subject invention provides advantageous fluorescent proteins. The invention also includes proteins substantially similar to, or mutants or variants of, the exemplified proteins.

Another aspect of the subject invention pertains to polynucleotide sequences that encode the detectable proteins of the present invention. In one embodiment, the present invention provides polynucleotide constructs comprising cDNA encoding novel colored and/or fluorescent proteins and mutants thereof.

In one embodiment, the invention provides nucleotide sequences of the inserts in pGEM-T vector (Promega), the conceptual translations of these inserts, and special properties of purified protein products.

The proteins and polynucleotides of the present invention can be used as described herein as colored and/or fluorescent (detectable) labels in a variety of ways, including but not limited to, as reporter genes for monitoring gene expression in living organisms, as protein tags for tracing the location of proteins within living cells and organisms, as reporter molecules for engineering various protein-based biosensors, and as genetically encoded pigments for modifying color and/or fluorescence of living organisms or their parts.

In a specific embodiment, the proteins of the subject invention can be used in molecular fluorescent tagging whereby the coding region of a protein of interest is fused with the coding region for a fluorescent protein of the subject invention. The product of such a gene shows the functional characteristics of the protein of interest, but bears the fluorescent label allowing tracing its movements.

Advantageously, the present invention provides proteins and polynucleotides to improve on the current technology of labeling and detection by offering a wider choice of colors and biochemical features never before provided by GFP and its modified variants.

BRIEF DESCRIPTION OF THE SEQUENCES

Figure 1:
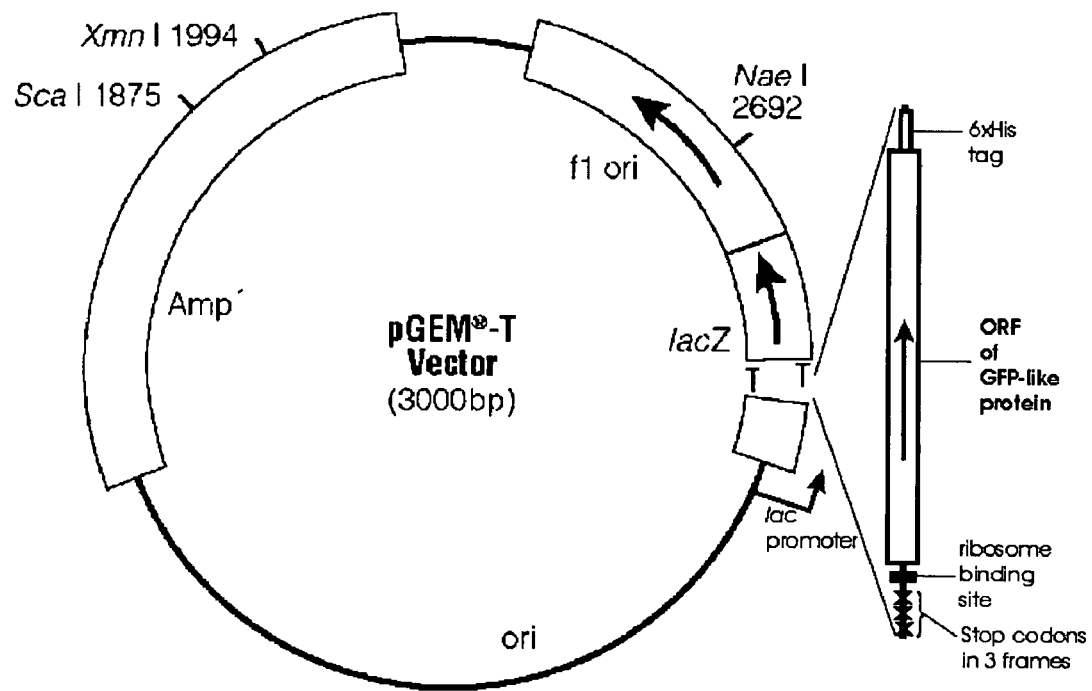
FIG. 1 shows the design of bacterial expression constructs for the proteins of interests of the present invention.
Figure 2:
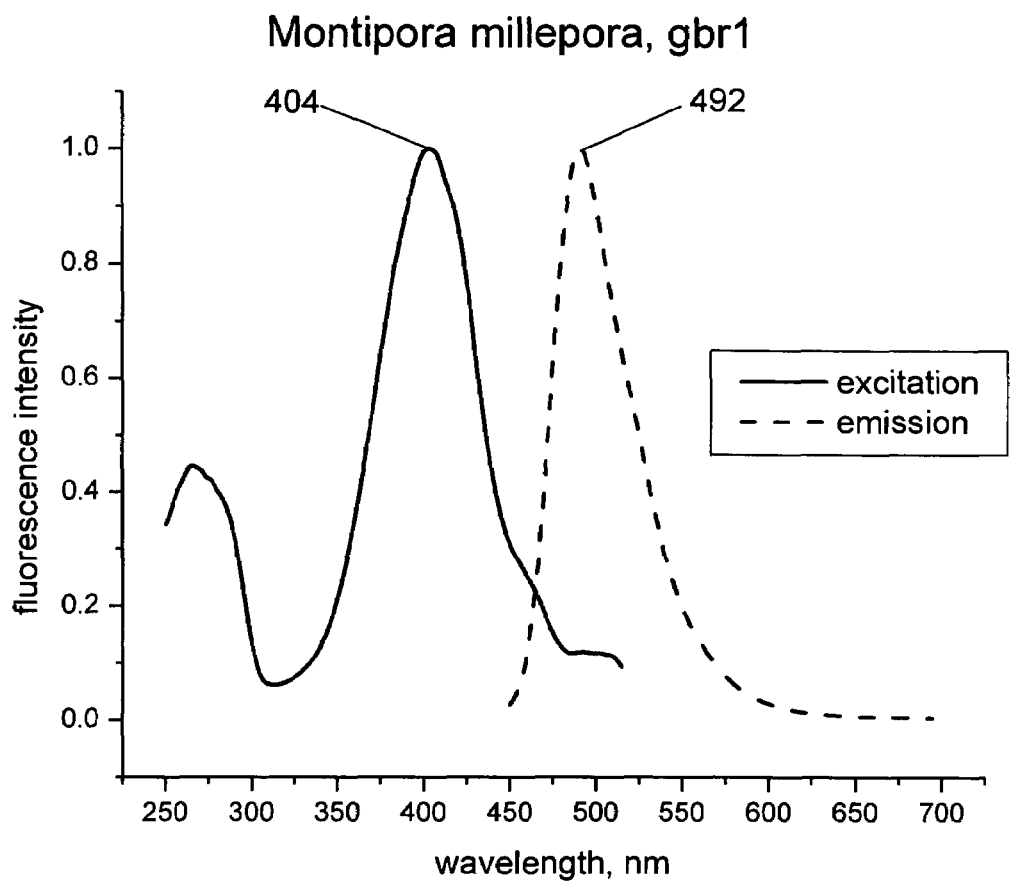
FIG. 2 shows the excitation and emission spectrum of *Montipora millepora*, gbr1.
Figure 3:
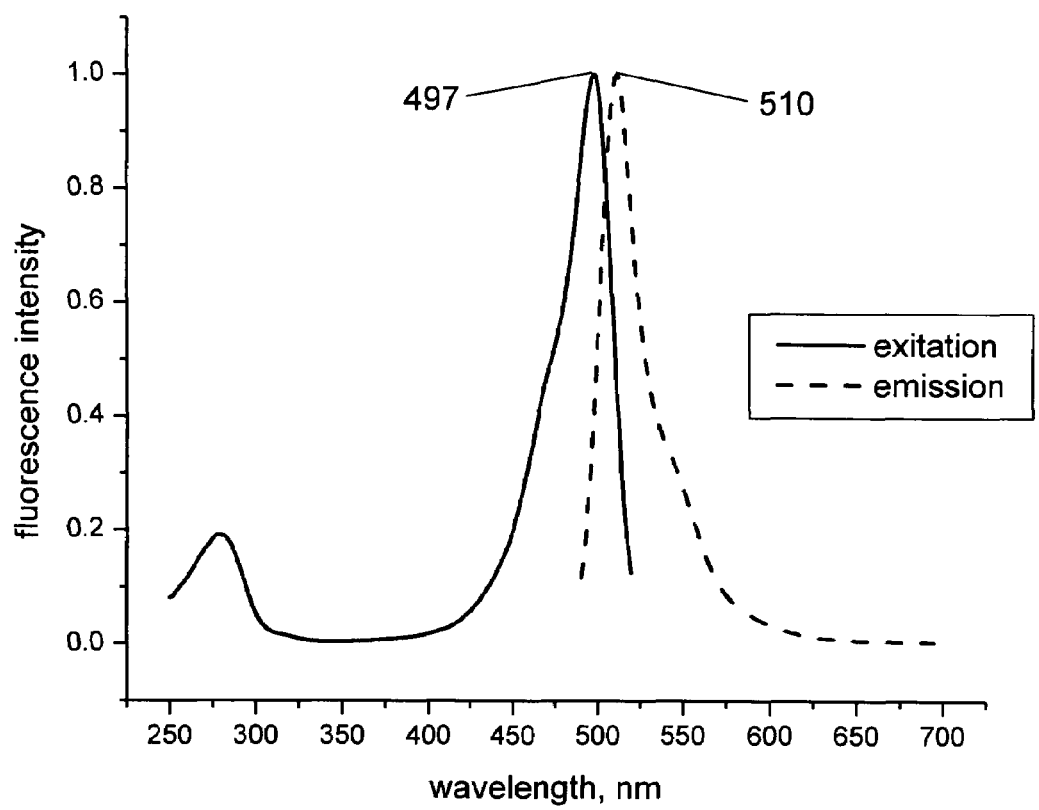
FIG. 3 shows the excitation and emission spectrum of *Echinophyllia echinata*, gbr3.
Figure 4:
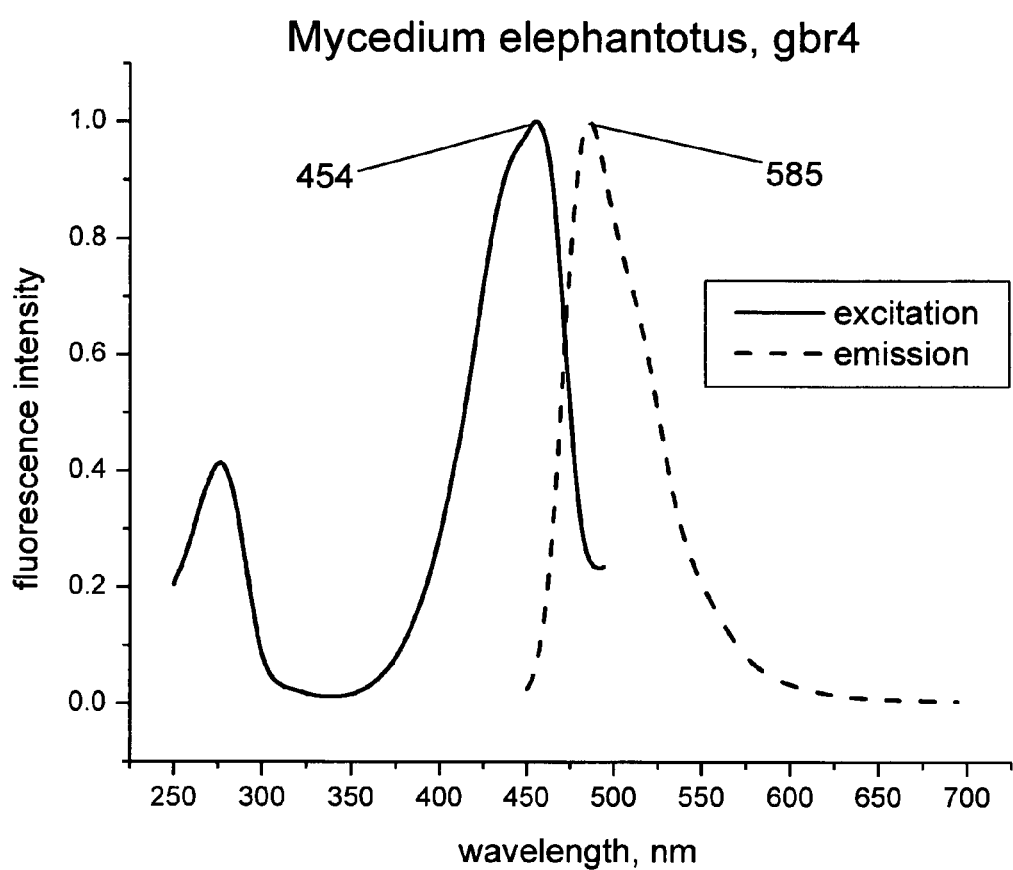
FIG. 4 shows the excitation and emission spectra of *Mycedium elephantotus*, gbr4.
Figure 5:
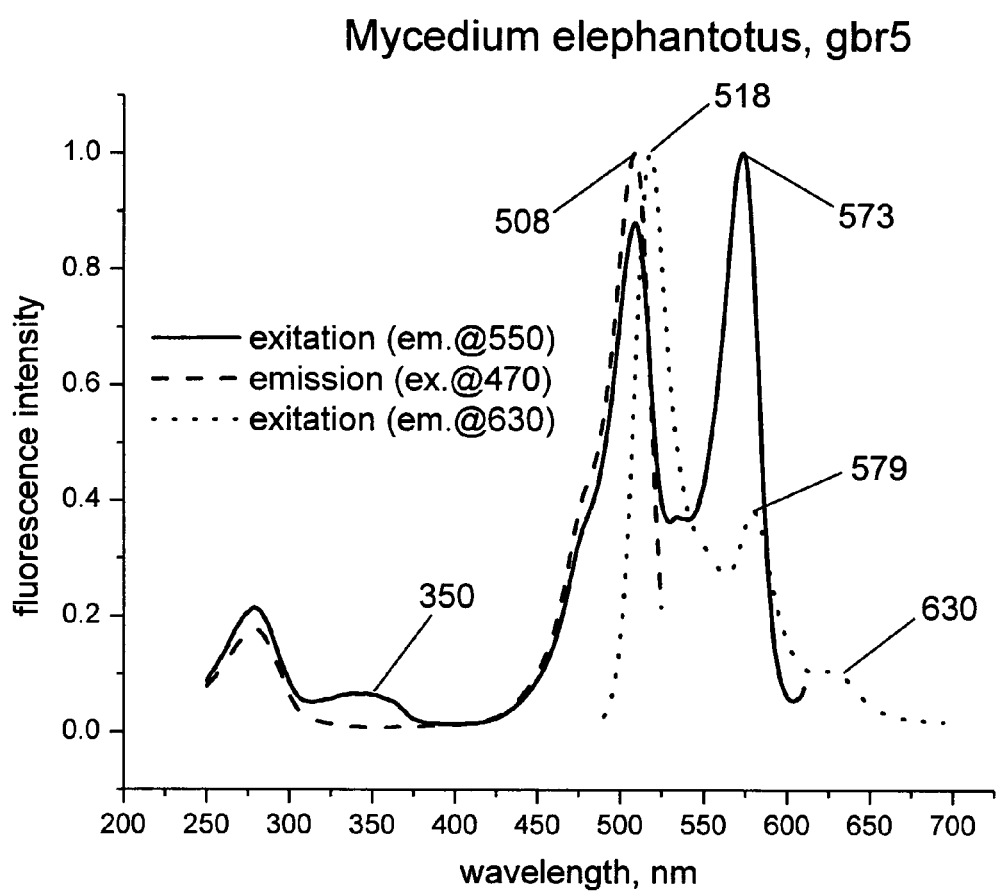
FIG. 5 shows the excitation and emission spectra of *Mycedium elephantotus*, gbr5.
Figure 6:
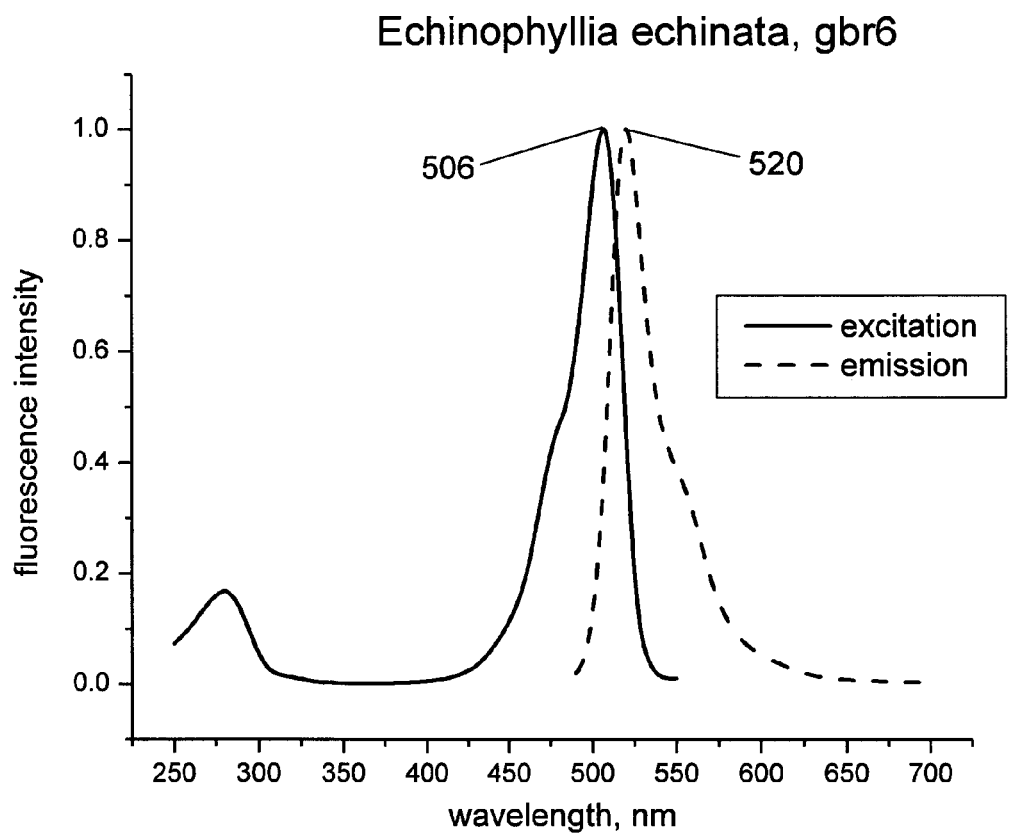
FIG. 6 shows the excitation and emission spectra of *Echinophyllia echinata*, gbr6.
Figure 7:
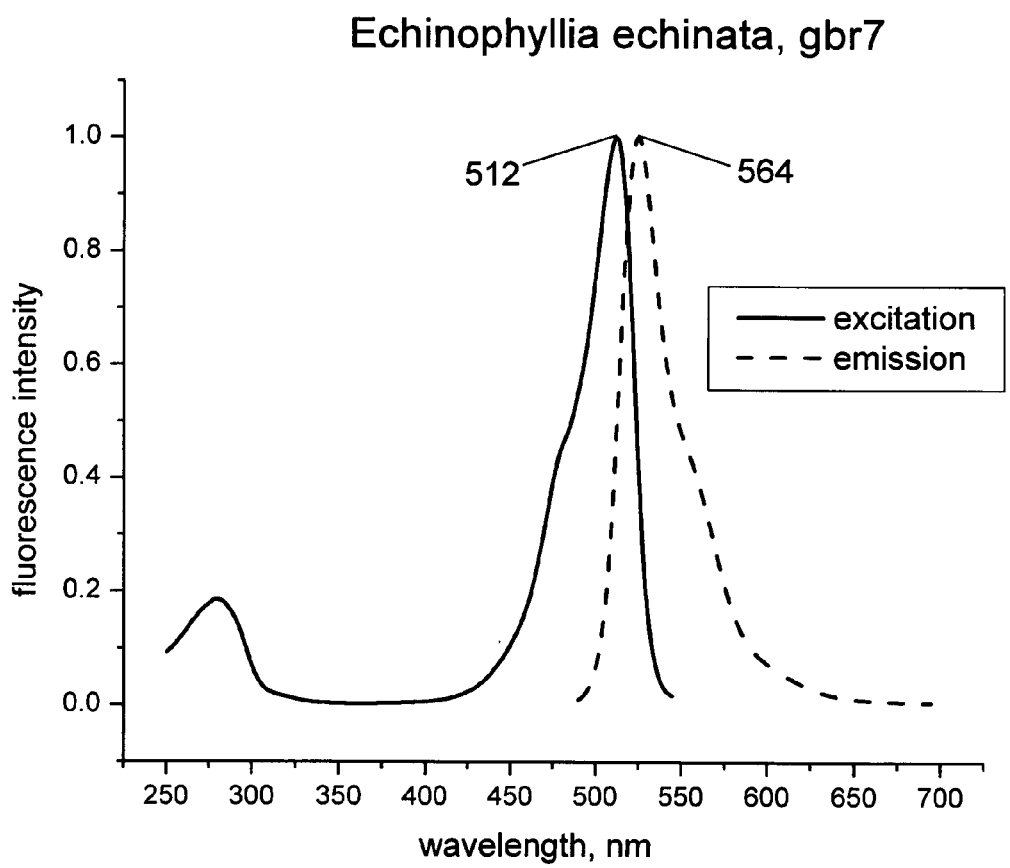
FIG. 7 shows the excitation and emission spectra of *Echinophyllia echinata*, gbr7.
Figure 8:
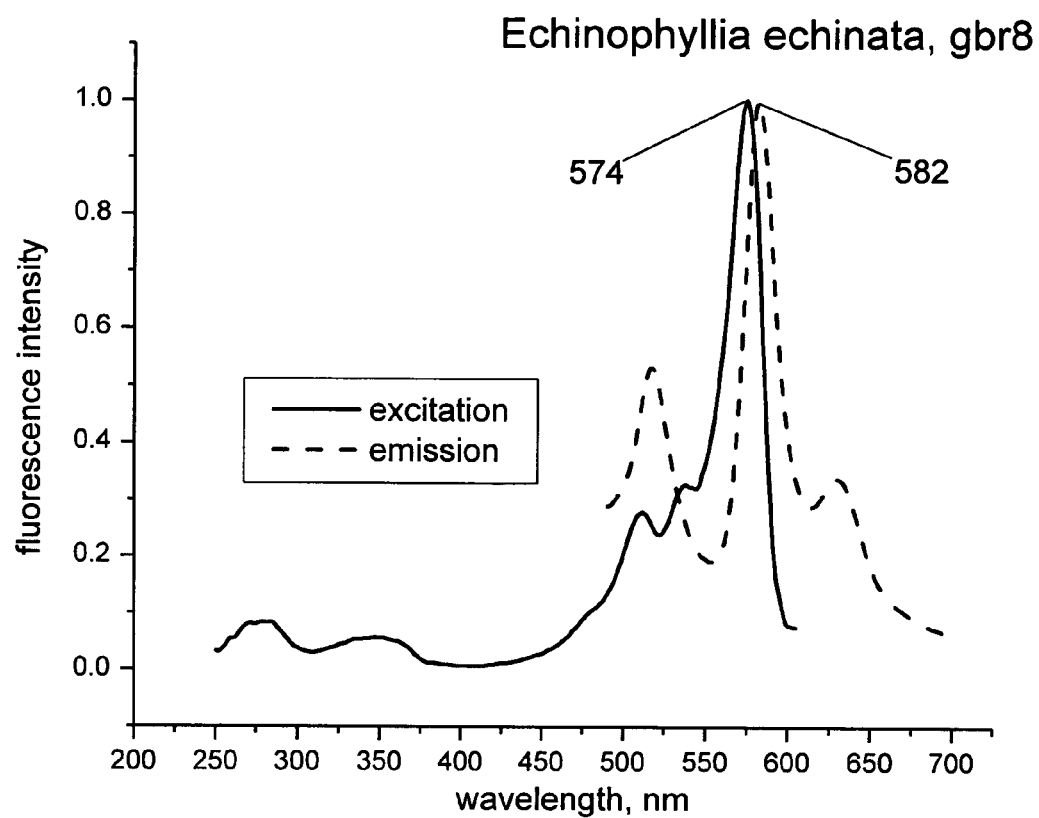
FIG. 8 shows the excitation and emission spectra of *Echinophyllia echinata*, gbr8.
Figure 9:
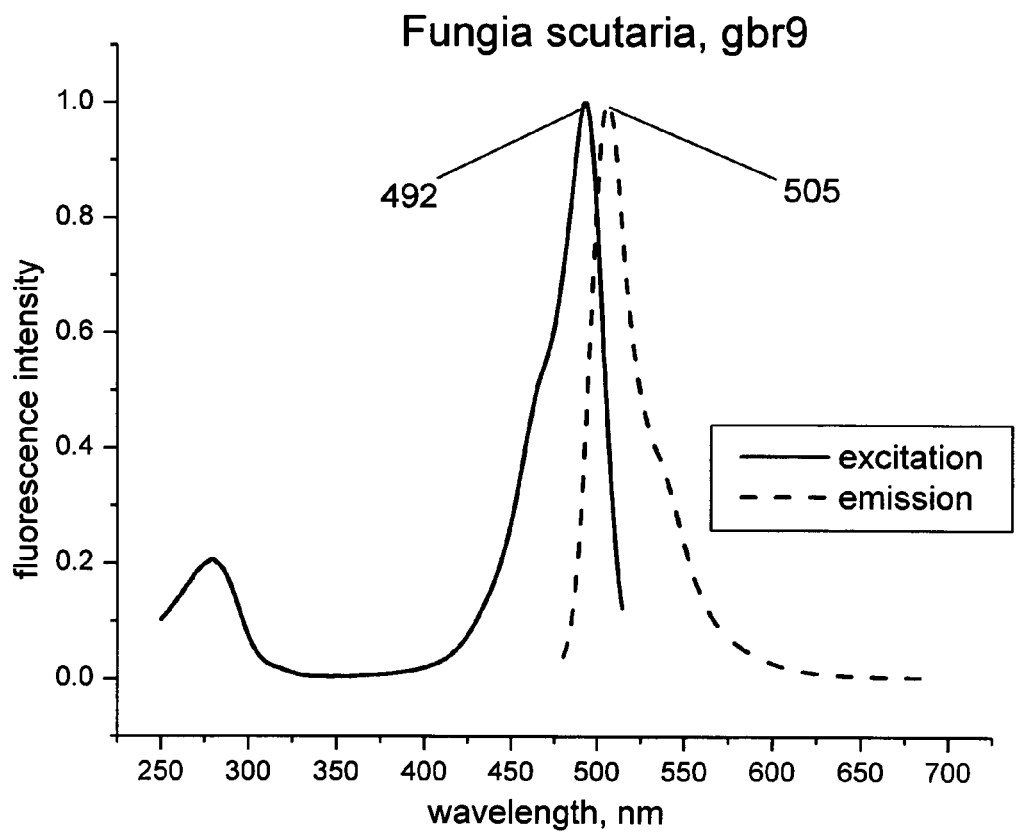
FIG. 9 shows the excitation and emission spectra of *Fungia scutaria*, gbr9.
Figure 10:
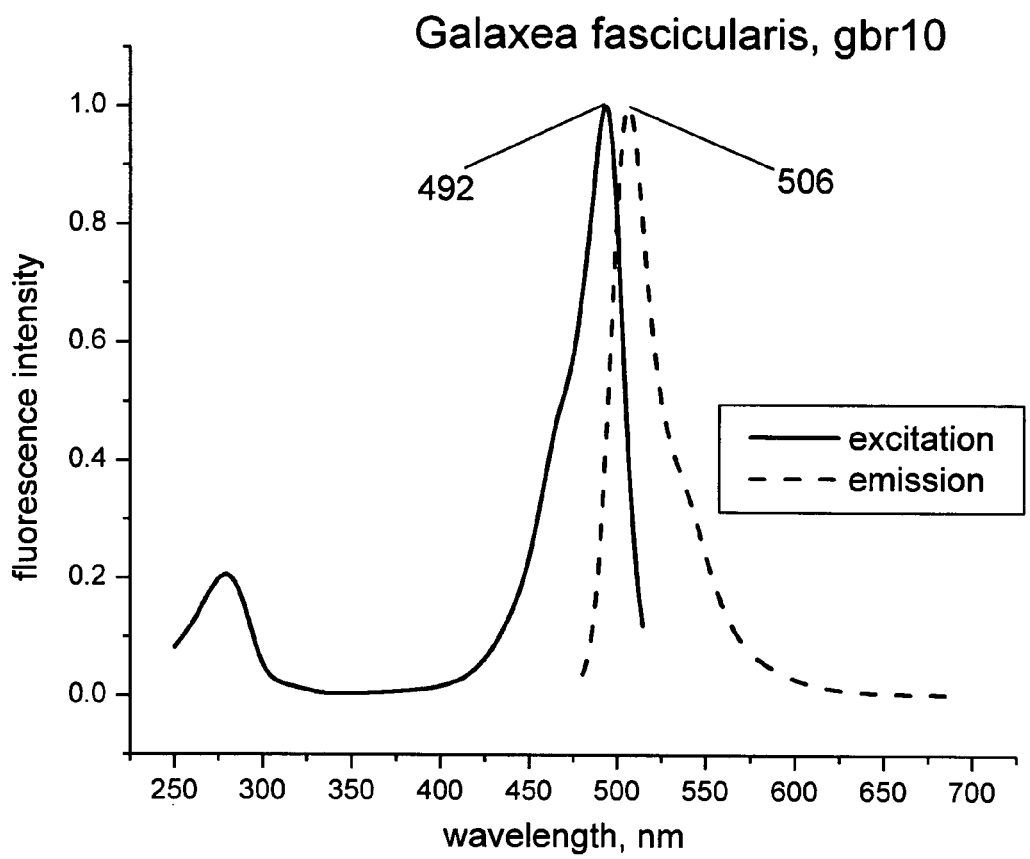
FIG. 10 shows the excitation and emission spectra of *Galaxea fascicularis*, gbr10.
Figure 11:
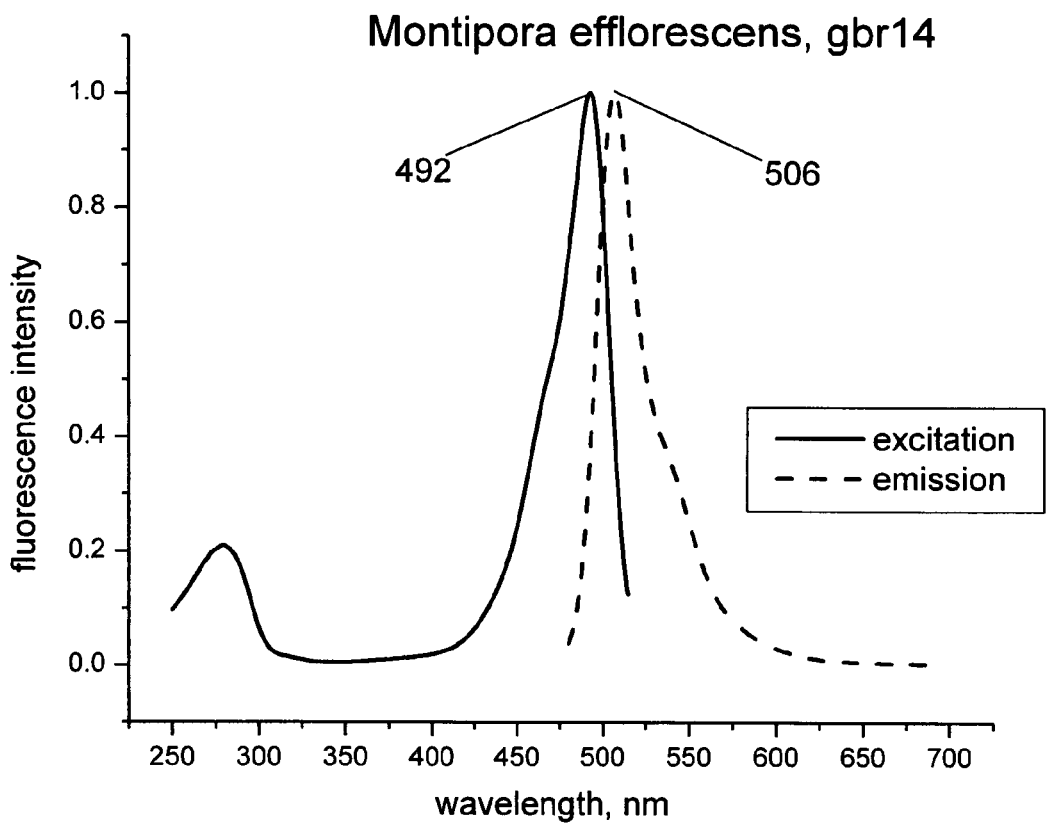
FIG. 11 shows the excitation and emission spectra of *Montipora efflorescens*, gbr14.
Figure 12:
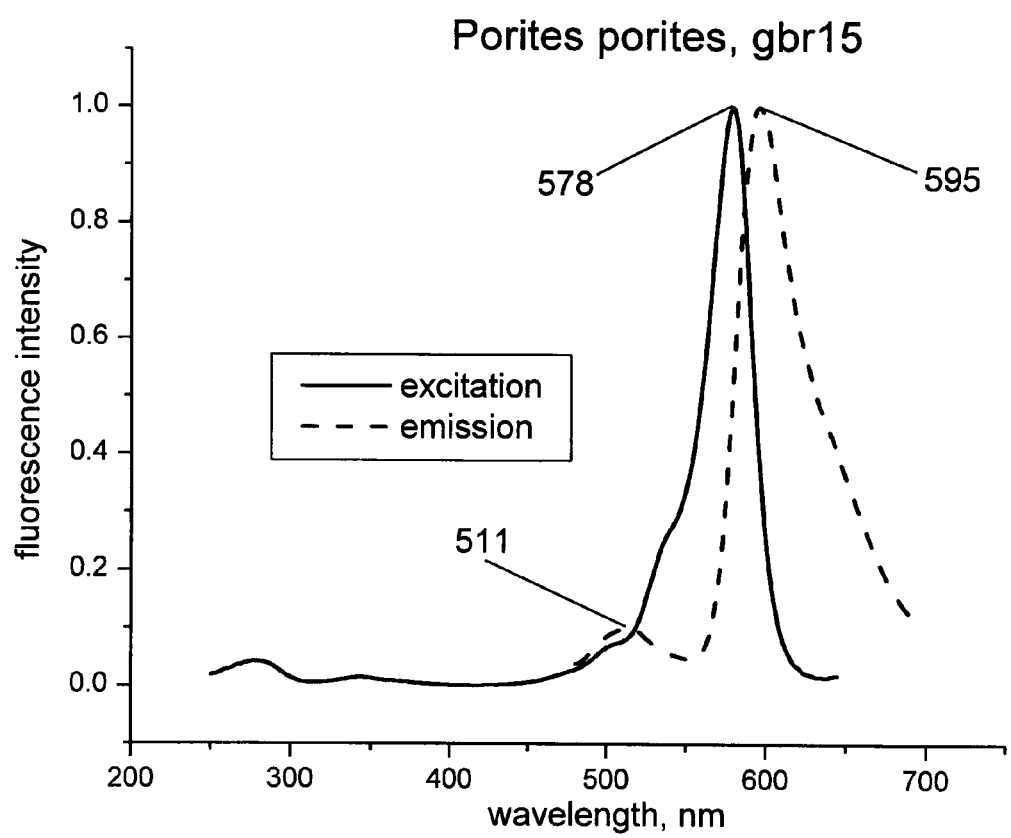
FIG. 12 shows the excitation and emission spectra of *Porites porites*, gbr15.
Figure 13:
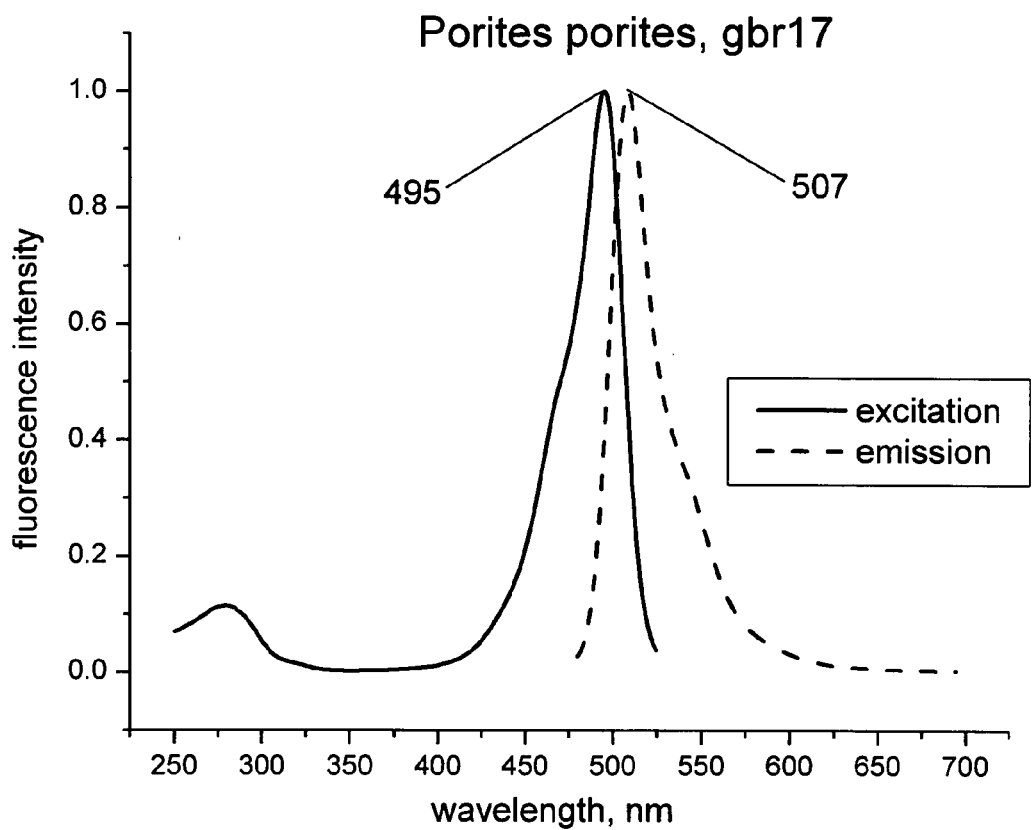
FIG. 13 shows the excitation and emission spectra of *Porites porites*, gbr17.
Figure 14:
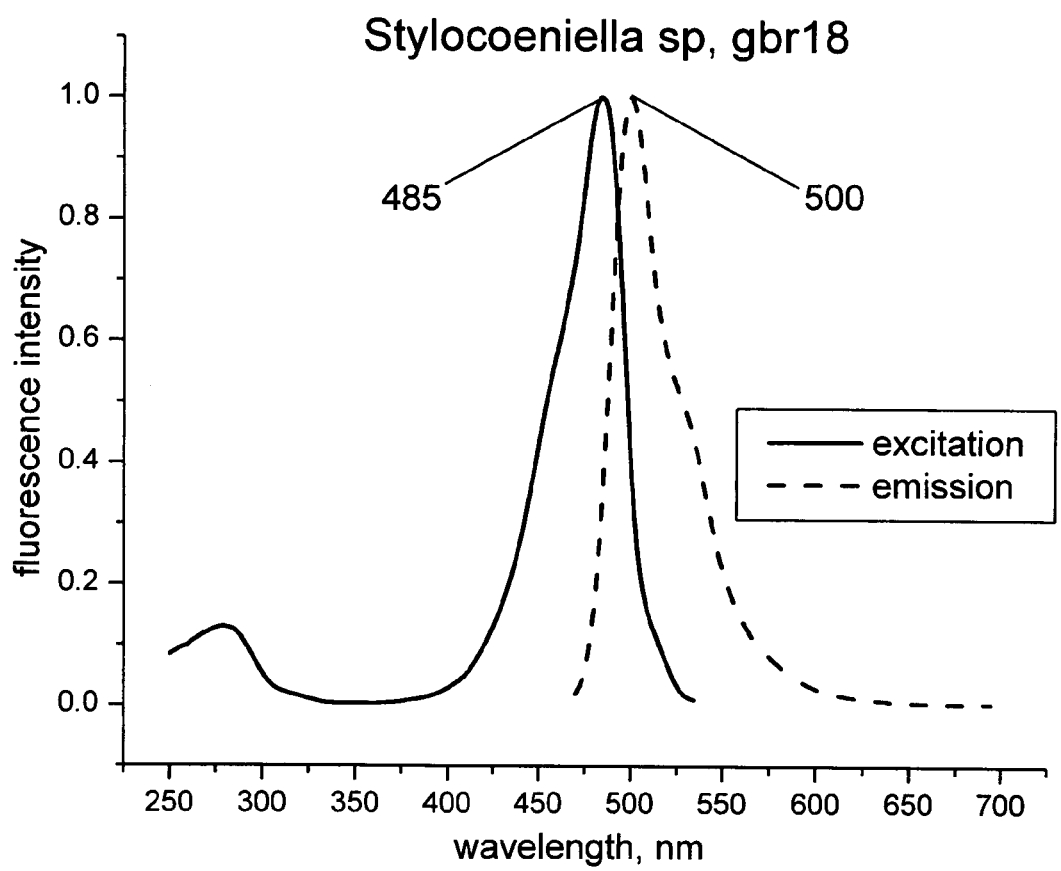
FIG. 14 shows the excitation and emission spectra of *Stylocoeniella* sp., gbr18.
Figure 15:
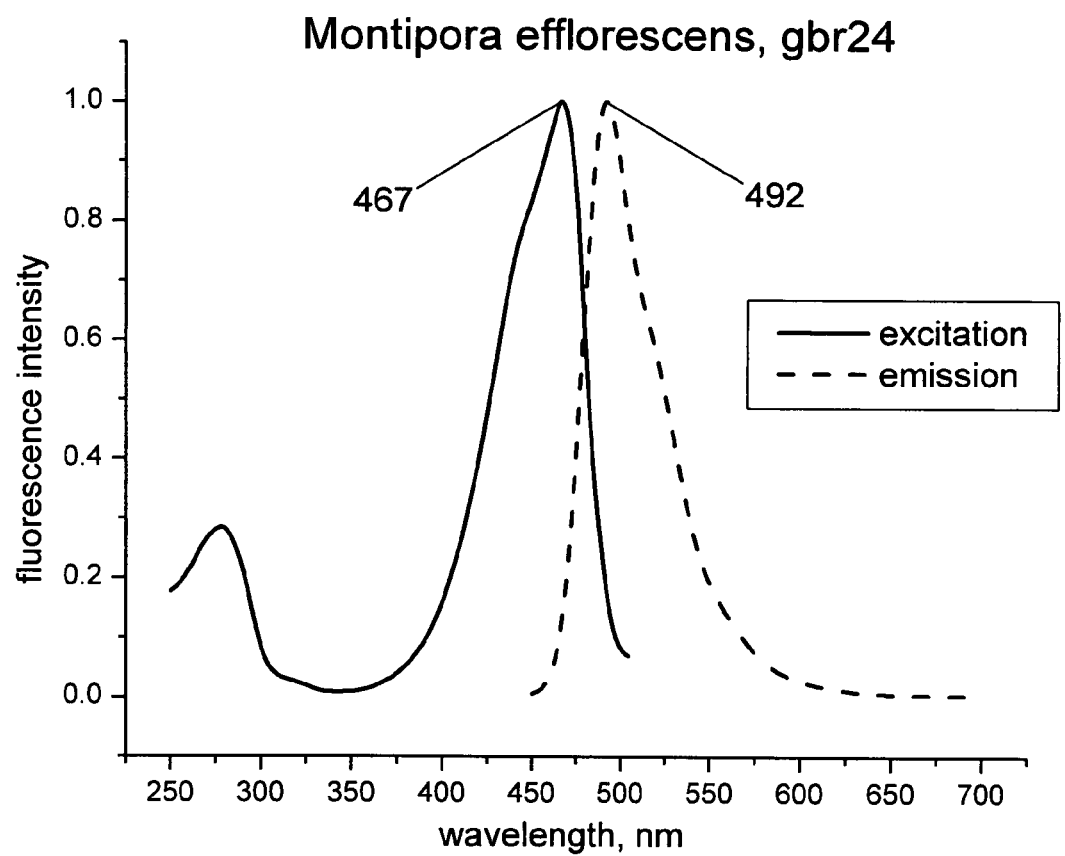
FIG. 15 shows the excitation and emission spectra of *Montipora efflorescens*, gbr24.
Figure 16:
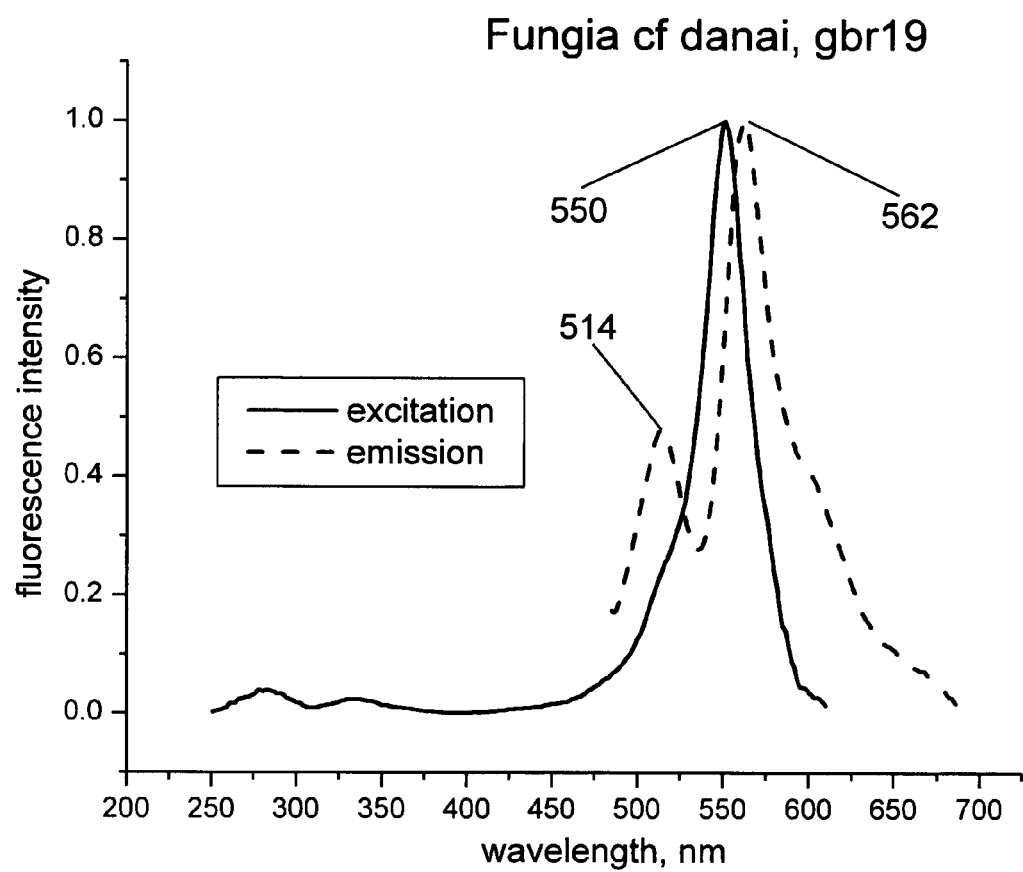
FIG. 16 shows the excitation and emission spectra of *Fungia cf danai*, gbr19.
Figure 17:
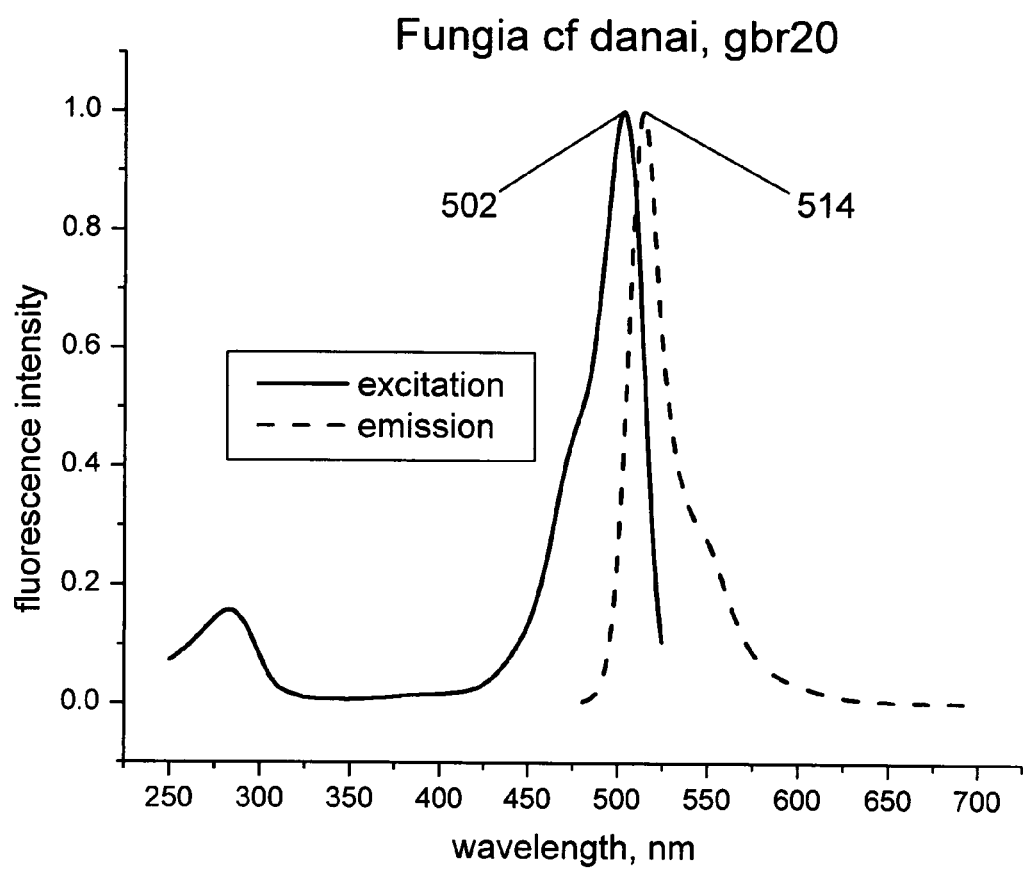
FIG. 17 shows the excitation and emission spectra of *Fungia cf danai*, gbr20.
Figure 18:
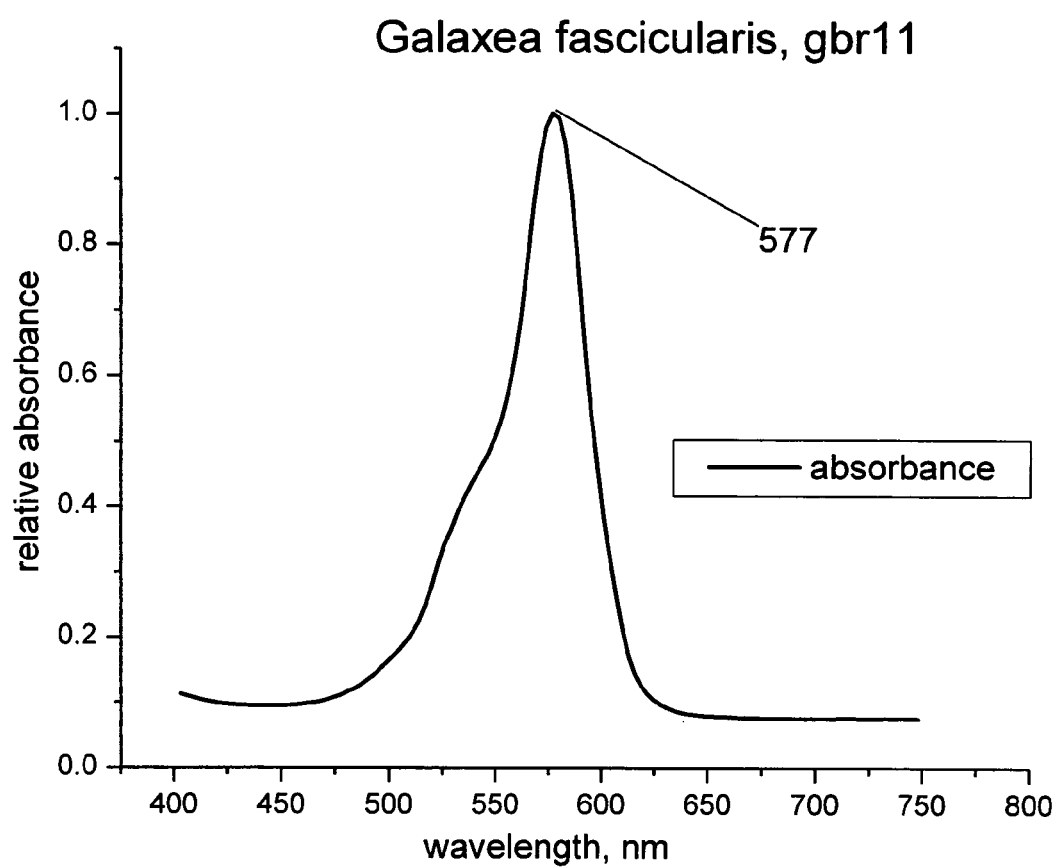
FIG. 18 shows the excitation and emission spectra of *Galaxea fascicularis*, gbr11.
Figure 19:
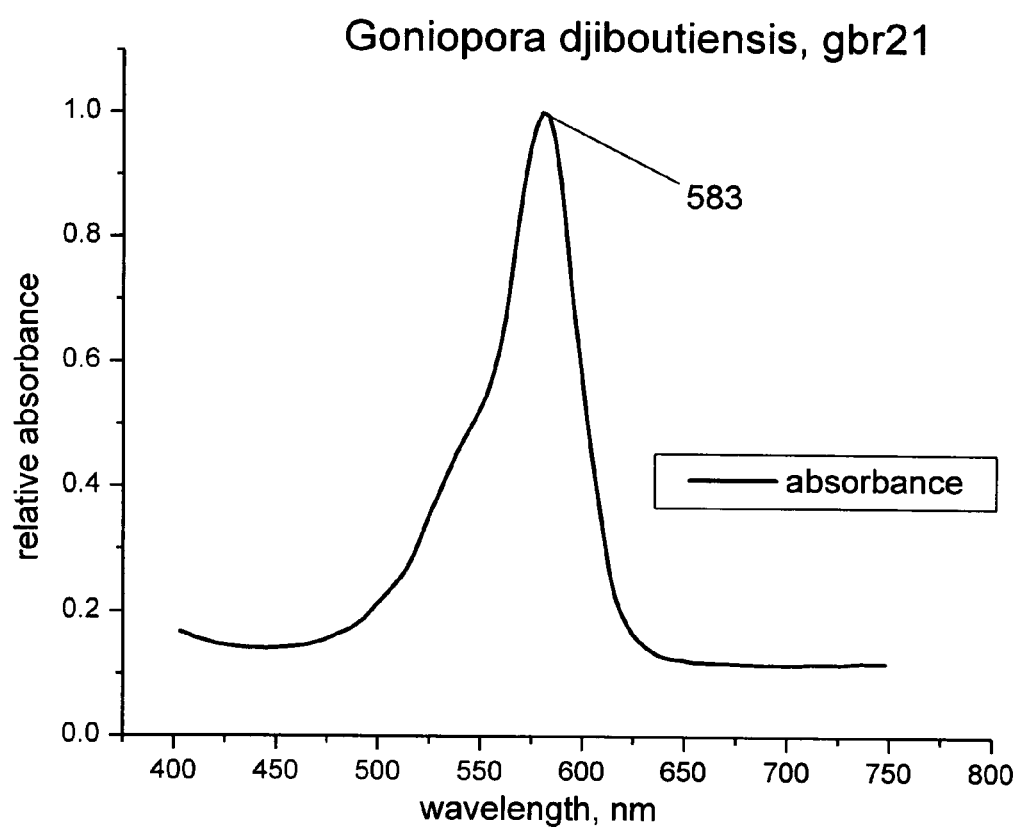
FIG. 19 shows the excitation and emission spectra of *Goniopora djiboutiensis*, gbr21.
Figure 20:
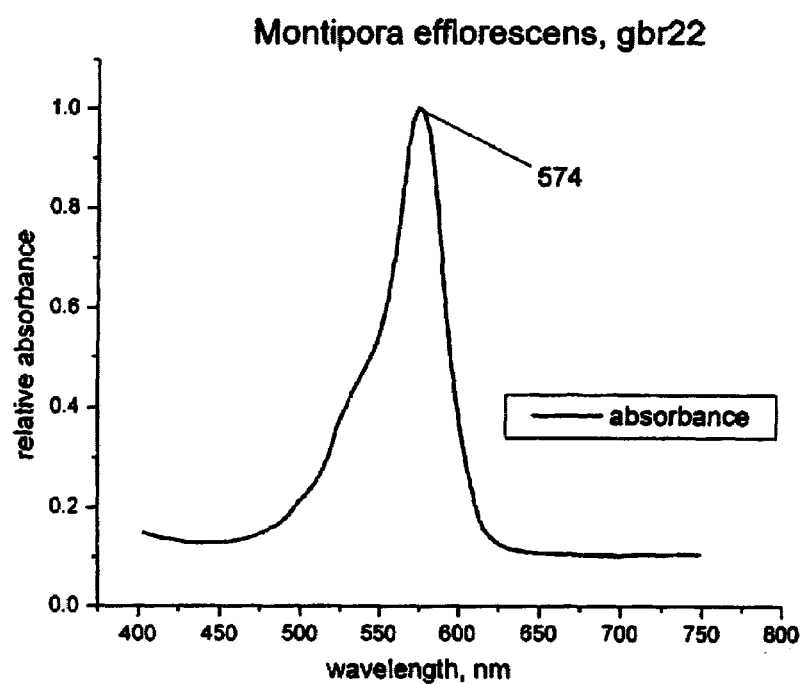
FIG. 20 shows the excitation and emission spectra of *Montipora efflorescens*, gbr22.
Figure 21:
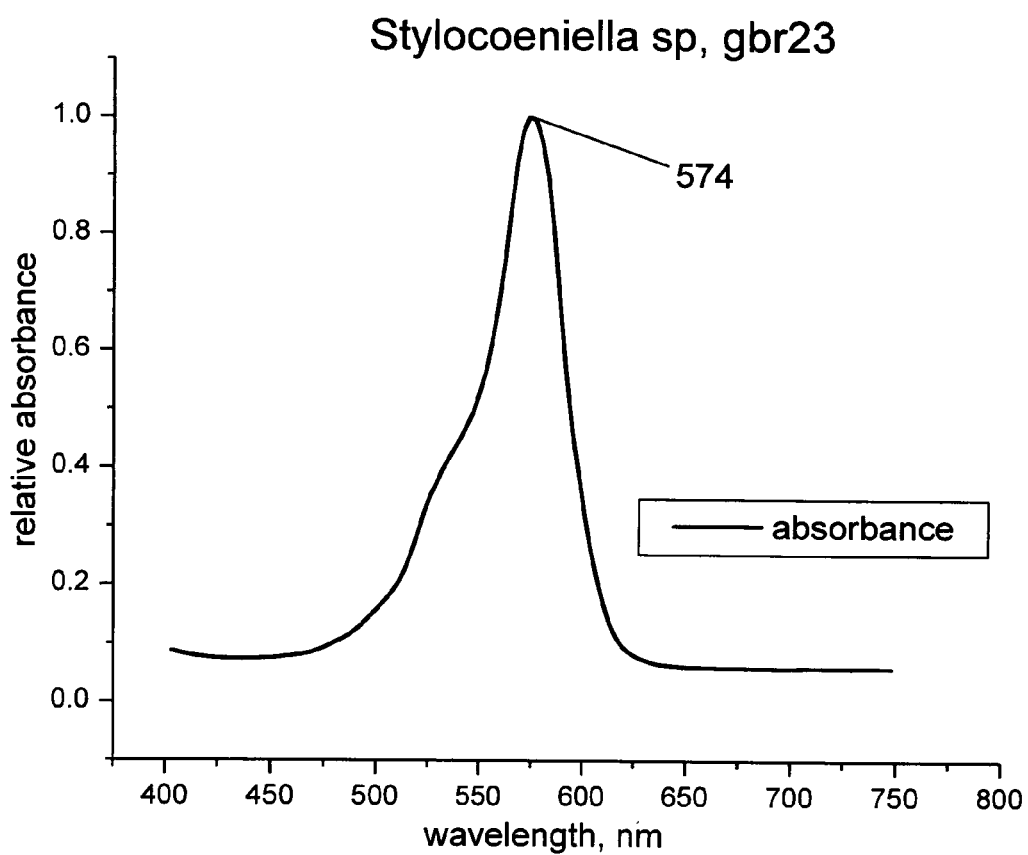
FIG. 21 shows the excitation and emission spectra of *Stylocoeriella* sp., gbr23.

SEQ ID NO:1 is the 5' heel of an upstream primer used according to the subject invention.

SEQ ID NO:2 is the 5' heel of a downstream primer used according to the subject invention.

SEQ ID NO:3 is the open reading frame of the cDNA encoding the gbr1 protein of interest from *Montipora millepora*. Parts of the sequence that have been artificially added during the cloning process to facilitate gene expression in *E. coli* are identified in misc_feature.

SEQ ID NO:4 is the open reading frame of the cDNA encoding the gbr3 protein of interest from *Echinophyllia echinata*. Parts of the sequence that have been artificially added during the cloning process to facilitate gene expression in *E. coli* are identified in misc_feature.

SEQ ID NO:5 is the open reading frame of the cDNA encoding the gbr4 protein of interest from *Mycedium elephantotus*. Parts of the sequence that have been artificially added during the cloning process to facilitate gene expression in *E. coli* are identified in misc_feature.

SEQ ID NO:6 is the open reading frame of the cDNA encoding the gbr5 protein of interest from *Mycedium elephantotus*. Parts of the sequence that have been artificially added during the cloning process to facilitate gene expression in *E. coli* are identified in misc_feature.

SEQ ID NO:7 is the open reading frame of the cDNA encoding the gbr6 protein of interest from *Echinophyllia echinata*. Parts of the sequence that have been artificially added during the cloning process to facilitate gene expression in *E. coli* are identified in misc_feature. A sequence identified in another misc_feature is derived from the cloning vector pGEM-T; it is included since in this particular construct it becomes translated during protein expression.

SEQ ID NO:8 is the open reading frame of the cDNA encoding the gbr7 protein of interest from *Echinophyllia echinata*. Parts of the sequence that have been artificially added during the cloning process to facilitate gene expression in *E. coli* are identified in misc_feature.

SEQ ID NO:9 is the open reading frame of the cDNA encoding the gbr8 protein of interest from *Echinophyllia echinata*. Parts of the sequence that have been artificially added during the cloning process to facilitate gene expression in *E. coli* are identified in misc_feature.

SEQ ID NO:10 is the open reading frame of the cDNA encoding the gbr9 protein of interest from *Fungia scutaria*. Parts of the sequence that have been artificially added during the cloning process to facilitate gene expression in *E. coli* are identified in misc_feature.

SEQ ID NO:11 is the open reading frame of the cDNA encoding the gbr10 protein of interest from *Galaxea fascicularis*. Parts of the sequence that have been artificially added during the cloning process to facilitate gene expression in *E. coli* are identified in misc_feature.

SEQ ID NO:12 is the open reading frame of the cDNA encoding the gbr11 protein of interest from *Galaxea fascicularis*. Parts of the sequence that have been artificially added during the cloning process to facilitate gene expression in *E. coli* are identified in misc_feature.

SEQ ID NO:13 is the open reading frame of the cDNA encoding the gbr14 protein of interest from *Montipora efflorescens*. Parts of the sequence that have been artificially added during the cloning process to facilitate gene expression in *E. coli* are identified in misc_feature.

SEQ ID NO:14 is the open reading frame of the cDNA encoding the gbr15 protein of interest from *Porites porites*. Parts of the sequence that have been artificially added during the cloning process to facilitate gene expression in *E. coli* are identified in misc_feature.

SEQ ID NO:15 is the open reading frame of the cDNA encoding the gbr17 protein of interest from *Porites porites*. Parts of the sequence that have been artificially added during the cloning process to facilitate gene expression in *E. coli* are identified in misc_feature.

SEQ ID NO:16 is the open reading frame of the cDNA encoding the gbr18 protein of interest from *Stylocoeniella* sp. Parts of the sequence that have been artificially added during the cloning process to facilitate gene expression in *E. coli* are identified in misc_feature.

SEQ ID NO:17 is the open reading frame of the cDNA encoding the gbr19 protein of interest from *Fungia cf danai*. Parts of the sequence that have been artificially added during the cloning process to facilitate gene expression in *E. coli* are identified in misc_feature.

SEQ ID NO:18 is the open reading frame of the cDNA encoding the gbr20 protein of interest from *Fungia cf danai*. Parts of the sequence that have been artificially added during the cloning process to facilitate gene expression in *E. coli* are identified in misc_feature. SEQ ID NO:19 is the open reading frame of the cDNA encoding the gbr21 protein of interest from *Goniopora djiboutiensis*. Parts of the sequence that have been artificially added during the cloning process to facilitate gene expression in *E. coli* are identified in misc_feature.

SEQ ID NO:20 is the open reading frame of the cDNA encoding the gbr22 protein of interest from *Montipora efflorescens*. Parts of the sequence that have been artificially added during the cloning process to facilitate gene expression in *E. coli* are identified in misc_feature.

SEQ ID NO:21 is the open reading frame of the cDNA encoding the gbr23 protein of interest from *Stylocoeniella* sp. Parts of the sequence that have been artificially added during the cloning process to facilitate gene expression in *E. coli* are identified in misc_feature.

SEQ ID NO:22 is the open reading frame of the cDNA encoding the gbr24 protein of interest from *Montipora efflorescens*. Parts of the sequence that have been artificially added during the cloning process to facilitate gene expression in *E. coli* are identified in misc_feature.

SEQ ID NO:23 is the open reading frame of the cDNA encoding the gbr25 protein of interest from *Montipora efflorescens*. Parts of the sequence that have been artificially added during the cloning process to facilitate gene expression in *E. coli* are identified in misc_feature.

SEQ ID NO:24 is the amino acid sequence encoded by SEQ ID NO:3.

SEQ ID NO:25 is the amino acid sequence encoded by SEQ ID NO:4.

SEQ ID NO:26 is the amino acid sequence encoded by SEQ ID NO:5.

SEQ ID NO:27 is the amino acid sequence encoded by SEQ ID NO:6.

SEQ ID NO:28 is the amino acid sequence encoded by SEQ ID NO:7.

SEQ ID NO:29 is the amino acid sequence encoded by SEQ ID NO:8.

SEQ ID NO:30 is the amino acid sequence encoded by SEQ ID NO:9.

SEQ ID NO:31 is the amino acid sequence encoded by SEQ ID NO:10.

SEQ ID NO:32 is the amino acid sequence encoded by SEQ ID NO:11.

SEQ ID NO:33 is the amino acid sequence encoded by SEQ ID NO:12.

SEQ ID NO:34 is the amino acid sequence encoded by SEQ ID NO:13.

SEQ ID NO:35 is the amino acid sequence encoded by SEQ ID NO:14.

SEQ ID NO:36 is the amino acid sequence encoded by SEQ ID NO:15.

SEQ ID NO:37 is the amino acid sequence encoded by SEQ ID NO:16.

SEQ ID NO:38 is the amino acid sequence encoded by SEQ ID NO:17.

SEQ ID NO:39 is the amino acid sequence encoded by SEQ ID NO:18.

SEQ ID NO:40 is the amino acid sequence encoded by SEQ ID NO:19.

SEQ ID NO:41 is the amino acid sequence encoded by SEQ ID NO:20.

SEQ ID NO:42 is the amino acid sequence encoded by SEQ ID NO:21.

SEQ ID NO:43 is the amino acid sequence encoded by SEQ ID NO:22.

SEQ ID NO:44 is the amino acid sequence encoded by SEQ ID NO:23.

DETAILED DESCRIPTION OF THE INVENTION

The present invention provides novel fluorescent and colored proteins isolated from marine organisms. In a particularly preferred embodiment, these proteins are fluorescent proteins. Specifically, exemplified herein are novel fluorescent proteins.

The subject invention further provides polynucleotide sequences encoding these proteins. These polynucleotide sequences include open reading frames encoding the specific exemplified detectable proteins, as well as expression constructs for expressing these proteins, for example, in bacterial hosts.

The proteins of the present invention can be readily, expressed by any one of the recombinant technology methods known to those skilled in the art having the benefit of the instant disclosure. The preferred method will vary depending upon many factors and considerations, including the host, and the cost and availability of materials and other economic considerations. The optimum production procedure for a given situation will be apparent to those skilled in the art having the benefit of the current disclosure.

The subject invention also concerns cells transformed with a polynucleotide of the present invention comprising a nucleotide sequences encoding a novel detectable protein. These cells may be prokaryotic or eukaryotic, plant or animal. In one embodiment, animals, such as fish, are transformed to provide them with a unique color or ability to fluoresce. Polynucleotides providing the markers of the present invention are stable in a diverse range of hosts, including prokaryotic and eukaryotic organisms, and the translation products are fully functional and capable of providing assayable characteristics.

In another embodiment, the present invention provides methods to synthesize colored and fluorescent proteins in a recombinant cell.

In a specific embodiment, the proteins of the subject invention can be used in molecular fluorescent tagging whereby the coding region of a protein of interest is fused with the coding region for a fluorescent protein of the subject invention. The product of such a gene shows the functional characteristics of the protein of interest, but bears the fluorescent label allowing tracing its movements. See, for example, Eichinger, L., S. S. Lee and M. Schleicher (1999) "Dictyostelium as model system for studies of the actin cytoskeleton by molecular genetics" *Microsc Res Tech* 47:124–134; Falk, M. M. and U. Lauf (2001) "High resolution, fluorescence deconvolution microscopy and tagging with the autofluorescent tracers CFP, GFP, and YFP to study the structural composition of gap junctions in living cells" *Microsc Res Tech* 52:251–262; Kallal, L. and J. L. Benovic (2000) "Using green fluorescent proteins to study G-protein-coupled receptor localization and trafficking" Trends Pharmacol Sci 21:175–180; and Laird, D. W., K. Jordan, T. Thomas, H. Qin, P. Fistouris and Q. Shao (2001) "Comparative analysis and application of fluorescent protein-tagged connexins" Microsc Res Tech 52:263–272.

In a further embodiment, the subject invention concerns polynucleotides comprising an in-frame fusion of nucleotide sequences encoding multiple genetic markers. In one embodiment, the polynucleotides encode the genetic markers GUS, and a detectable protein of the subject invention.

The subject invention helps to provide a more abundant and diverse collection of proteins, which can be used in place of a GFP protein, such that new proteins are readily available for commercial exploitation by small companies that cannot take advantage of the current technology for financial reasons.

Definitions

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides.

As used herein, "a vector" is a DNA sequence having the elements necessary for the transcription/translation of a gene. Such elements would include, for example, promoters. Various classes of promoters are well known in the art and can be obtained commercially or assembled from the sequences and methods, which are also well known in the art. A number of vectors are available for expression and/or cloning, and include, but are not limited to, pBR322, pUC series, M13 series, and pBLUESCRIPT vectors (Stratagene, La Jolla, Calif.).

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Detectable Proteins

The subject invention provides novel fluorescent and/or colored proteins. The novel colored and fluorescent proteins of the present invention can be detected using standard long-wave UV light sources or, preferably, optical designs appropriate for detecting agents with the excitation/emission characteristics of the proteins exemplified herein (see, for example, FIGS. 2–21). These proteins are referred to herein as "detectable proteins" or "marker proteins." The interaction of two or more residues of the protein and external agents such as molecular oxygen give rise to the colored and/or fluorescent feature of the proteins.

Advantageously, the use of these proteins facilitate real-time detection in vivo, a substrate is not required, and the relatively small size make the proteins very advantageous.

Substitution of amino acids other than those specifically exemplified or naturally present in the genetic marker proteins of the invention are also contemplated within the scope of the present invention. Such substitutions will create "variant proteins" within the scope of the subject invention. Variants and fragments preferably have emission and excitation maxima within 10 nm of the values shown in FIGS. 2–21. For example, non-natural amino acids can be substituted for the amino acids of the marker proteins, so long as a marker protein having the substituted amino acids retains its ability to be detected through fluorescence and/or color. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a detectable protein used in the present invention are also encompassed within the scope of the invention.

Amino acids can be generally categorized in the following classes: non-polar, uncharged polar, basic, and acidic. Conservative substitutions whereby a marker protein having an amino acid of one class is replaced with another amino acid of the same class fall within the scope of the subject invention so long as a marker protein having the substitution still is detectable Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Polynucleotides cDNA sequences encoding the proteins of the present invention are provided. Polynucleotides of the present invention can be composed of either RNA or DNA. Preferably, the polynucleotides are composed of DNA. The subject invention also encompasses those polynucleotides that are complementary in sequence to the polynucleotides disclosed herein.

Specifically exemplified are DNA sequences that encode novel fluorescent proteins. These DNA sequences are set forth in SEQ. ID NOS. 3–23.

Sequences of the subject invention may utilize codons preferred for expression by the selected host strains. These sequences may also have sites for cleavage by restriction enzymes, and/or initial, terminal, or intermediate DNA sequences which facilitate construction of readily expressed vectors.

Because of the degeneracy of the genetic code, a variety of different polynucleotide sequences can encode the detectable proteins of the present invention. In addition, it is well within the skill of a person trained in the art to create alternative polynucleotide sequences encoding the same, or essentially the same, detectable proteins of the subject invention. These variant or alternative polynucleotide sequences are within the scope of the subject invention. As used herein, references to "essentially the same" sequence refers to sequences which encode amino acid substitutions, deletions, additions, or insertions which do not eliminate the detectability of the polypeptide encoded by the polynucleotides of the present invention. Allelic variants of the nucleotide sequences encoding a genetic marker protein of the invention are also encompassed within the scope of the invention.

The subject invention also concerns variants of the polynucleotides of the present invention that encode detectable proteins. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Polynucleotides and polypeptides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used.

The subject invention also contemplates those polynucleotide molecules having sequences that are sufficiently homologous with the polynucleotide sequences exemplified herein so as to permit hybridization with that sequence under standard stringent conditions and standard methods (Maniatis et al. 1982). As used herein, "stringent" conditions for hybridization refers to conditions wherein hybridization is typically carried out overnight at 20–25 C below the melting temperature (Tm) of the DNA hybrid in 6× SSPE, 5× Denhardt's solution, 0.1% SDS, 0.1 mg/ml denatured DNA. The melting temperature, Tm, is described by the following formula (Beltz et al., 1983):

$$Tm=81.5\ C+16.6\ \text{Log}\ [Na+]+0.41(\%\ G+C)-0.61(\%\ \text{formamide})-600/\text{length of duplex in base pairs}.$$

Washes are typically carried out as follows:

(1) Twice at room temperature for 15 minutes in 1× SSPE, 0.1% SDS (low stringency wash).

(2) Once at Tm−20 C for 15 minutes in 0.2× SSPE, 0.1% SDS (moderate stringency wash).

The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. The polynucleotide sequence includes both the sense and antisense strands either as individual strands or in the duplex.

Recombinant Hosts

Polynucleotide molecules containing DNA sequences encoding the colored and/or fluorescent proteins of the present invention can be introduced into a variety of host cells including bacterial cells, yeast cells, fungal cells, plant cells and animal cells. Methods by which the exogenous genetic material can be introduced into such host cells are well known in the art.

In one embodiment, the invention provides a bacteria cell capable of expressing the novel colored and fluorescent proteins.

Plants, plant tissues, and plant cells bred to contain, or transformed with, a polynucleotide of the invention are also contemplated by the present invention. In one embodiment, the polynucleotide encodes a detectable polypeptide shown in SEQ ID NOS. 7–10, or a functional fragment or variant thereof. Plants within the scope of the present invention include monocotyledonous plants, such as rice, wheat, barley, oats, sorghum, maize, sugarcane, pineapple, onion, bananas, coconut, lilies, grasses, and millet; and dicotyledonous plants, such as peas, alfalfa, tomato, melon, chickpea, chicory, clover, kale, lentil, soybean, tobacco, potato, sweet potato, radish, cabbage, rape, apple trees, grape, cotton, sunflower, and lettuce; and conifers. Techniques for transforming plant cells with a gene are known in the art and include, for example, *Agrobacterium* infection, biolistic methods, electroporation, calcium chloride treatment, etc. Transformed cells can be selected, redifferentiated, and grown into plants using standard methods known in the art. The progeny of any transformed plant cells or plants are also included within the scope of the present invention.

The subject invention also concerns non-human transgenic animals which have incorporated into the host cell genome a polynucleotide of the invention. Methods for producing transgenic animals, including mice, rats, pigs, sheep, cows, fish, and the like are well known in the art.

The subject invention also concerns methods for isolating transformants expressing a transgene. In one embodiment, an expression construct of the present invention comprising a transgene of interest operably linked to a nucleotide sequence encoding a detectable marker of the present invention is used to transform a cell. Methods for transforming cells are well known in the art. Transformed cells expressing the transgene are selected by identifying those cells expressing a genetic marker of the invention.

Expression Constructs

An expression construct of the invention typically comprises a structural gene sequence (encoding a protein), an antisense sequence, or other polynucleotide sequences, or a site for insertion of such sequences, operably linked to a polynucleotide of the present invention encoding a marker. The structural gene can be a gene encoding a protein from a prokaryotic or eukaryotic organism, for example, a human, mammal, insect, plant, bacteria, or virus. Proteins that can be encoded by a gene sequence include, but are not limited to, enzymes, hormones, cytokines, interleukins, receptors, growth factors, immunoglobulins, transcription factors, and *Bacillus thuringiensis* (B.t.) crystal toxin proteins. Sequences encoding B.t. proteins which have codon usage for preferential expression in plants are described in U.S. Pat. Nos. 5,380,831; 5,567,862; 5,567,600; 6,013,523; and 6,015,891. An antisense sequence is a sequence wherein the RNA transcribed from the antisense sequence is at least partially complementary to RNA transcribed from a gene encoding a protein.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a marker of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

If the expression construct is to be provided in a plant cell, plant viral promoters, such as, for example, the cauliflower mosaic virus (CaMV) 35S (including the enhanced CaMV 35S promoter (see, for example U.S. Pat. No. 5,106,739)) or 19S promoter can be used. Plant promoters such as prolifera promoter, Ap3 promoter, heat shock promoters, T-DNA 1'- or 2'-promoter of *A. tumafaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are contemplated for use with the polynucleotides of the invention.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked mature polypeptide to a wide range of post-translational cellular destinations, ranging from a specific organelle compartment to sites of protein action and the extracellular environment. Targeting marker gene products to an intended cellular and/or extracellular destination through the use of operably linked signal peptide sequence is contemplated for use with the polypeptides of the invention. Enhancers are cis-acting elements that increase activity of a promoter and can also be included in the expression construct. Enhancer elements are known in the art, and include, but are not limited to, the CaMV 35S enhancer element, maize shrunken-1 enhancer element, cytomegalovirus (CMV) early promoter enhancer element, and the SV40 enhancer element.

DNA sequences which direct polyadenylation of the mRNA encoded by the structural gene can also be included in the expression construct. The expression constructs of the invention can also include a polynucleotide sequence that directs transposition of other genes, i.e., a transposon.

Applications

There are many ways in which the novel proteins of the subject invention can be used. In one embodiment, the proteins can be used to identify cells. In these methods the proteins can be used to express fluorescence in a cell. One use for this method is in pre-labeling isolated cells or a population of similar cells prior to exposing the cells to an environment in which different cell types are present. Detection of fluorescence in only the original cells allows the location of such cells to be determined and compared with the total population.

A second group of methods concerns the identification of cells that have been transformed with exogenous DNA of interest. Identifying cells transformed with exogenous DNA is required in many in vitro procedures as well as in in vivo applications such as gene therapy.

In one embodiment of the subject invention, a polynucleotide sequence encoding a protein of the subject invention is fused to a DNA sequence encoding a selected protein in order to directly label the encoded protein. Expressing such a fluorescent and/or colored protein in a cell results in the production of labeled proteins that can be readily detected. This is useful in confirming that a protein is being produced by a chosen host cell. It also allows the location of the selected protein to be determined.

Cells that have been transformed with exogenous DNA can also be identified without creating a fusion protein. Here, the method relies on the identification of cells that have received a plasmid or vector that comprises at least two transcriptional or translational units. A first unit encodes and directs expression of the desired protein, while the second unit encodes and directs expression of the detectable protein. Co-expression of the detectable protein from the second transcriptional or translational unit ensures that cells containing the vector are detected and differentiated from cells that do not contain the vector.

In methods to produce fluorescent molecular weight markers, a gene sequence is generally fused to one or more DNA sequences that encode proteins having defined amino acid sequences and the fusion proteins are expressed from an expression vector. Expression results in the production of fluorescent proteins of defined molecular weight or weights that may be used as markers (following calculation of the size of the complete amino acid sequence).

Amino acid replacements that produce different color forms permit simultaneous use of multiple reporter genes. Different colored proteins can be used to identify multiple cell populations in a mixed cell culture or to track multiple cell types, enabling differences in cell movement or migration to be visualized in real time without the need to add additional agents or fix or kill the cells.

Other options include tracking and determining the ultimate location of multiple proteins within a single cell, tissue or organism; differential promoter analysis in which gene expression from two different promoters is determined in the same cell, tissue or organism; and FACS sorting of mixed cell populations.

The techniques that can be used with spectrally separable proteins are exemplified by confocal microscopy, flow cytometry, and fluorescence activated cell sorting (FACS) using modular flow, dual excitation techniques.

In one embodiment, the subject invention concerns polynucleotides comprising an in-frame fusion of nucleotide sequences encoding multiple genetic markers. For example, a polynucleotide of the invention may comprise a first nucleotide sequence that is operably linked in-frame to a second nucleotide sequence. The polynucleotide encodes the amino acid sequences of the detectable protein and another genetic marker such that the genetic markers are in direct contact with one another, i.e., where the last amino acid of the fluorescent genetic marker is immediately contiguous with the first amino acid of the other genetic marker, or they can be separated by a peptide linker sequence, for example, as described in U.S. Pat. No. 5,891,680 and Li et al., 2001, that do not substantially alter functional activity of the genetic markers.

The subject invention also concerns kits comprising in one or more containers and a polynucleotide and/or protein of the present invention.

Additional useful applications of the technology described herein include, but are not limited to, the following:

FRET—Fluorescence Resonant Energy Transfer: This technique allows observation and quantification of molecular interactions. It requires at least two fluorescent proteins of different colors. Currently the most widely used pair is CFP and YFP (mutated variants of GFP); the proteins of the subject invention may be substituted for either or both of them.

REFERENCES

1. Hanson, M. R. and R. H. Kohler. 2001. GFP imaging: methodology and application to investigate cellular compartmentation in plants. *J Exp Bot* 52: 529–539.
2. Pollok, B. A. and R. Heim. 1999. Using GFP in FRET-based applications. *Trends Cell Biol* 9: 57–60.
3. Schuttrigkeit, T. A., U. Zachariae, T. von Feilitzsch, J. Wiehler, J. von Hummel, B. Steipe and M. E. Michel-Beyerle. 2001. Picosecond time-resolved FRET in the fluorescent protein from Discosoma Red (wt-DsRed). *Chemphyschem* 2: 325–328.
4. Hillisch, A., M. Lorenz and S. Diekmann. 2001. Recent advances in FRET: distance determination in protein-DNA complexes. *Curr Opin Struct Biol* 11: 201–207.

FRAP—Fluorescence Redistribution After Photobleaching: Tthis technique quantifies the dynamics of tagged molecules or the reporter molecules themselves. It involves in photobleaching (burning out) of all the fluorescent molecules within a small area by intense excitation light and monitoring the process of fluorescence recovery within this area (due to migration of tagged molecules from adjacent areas).

REFERENCES

1. Reits, E. A. and J. J. Neefjes. 2001. From fixed to FRAP: measuring protein mobility and activity in living cells. *Nat Cell Biol* 3: E145–147.

2. Houtsmuller, A. B. and W. Vermeulen. 2001. Macromolecular dynamics in living cell nuclei revealed by fluorescence redistribution after photobleaching. *Histochem Cell Biol* 115:13–21.

"Fluorescent timer" applications: one of the proteins exemplified herein—scubRFP—due to its natural spectroscopic properties, can be used as a reporter that changes color with time. Such reporters make it possible to estimate the time elapsed since the reporter protein was synthesized by quantifying its color. In addition, since the maturation speed (the rate of conversion from green to red) in scubRFP can be increased by UV-A light, it is possible to adjust its timing scale: experiments that need timing in shorter intervals may use appropriate background UV illumination to speed up the green-to-red conversion.

REFERENCES

1. Terskikh, A. V., A. Fradkov, A. Zaraiskiy, A. V. Kajava, M. Matz, S. Kim, I. Weissman and P. Siebert. 2000. "Fluorescent timer": Protein that changes color over time. *Molecular Biology of the Cell* 11: 648.
2. Verkhusha, V. V., H. Otsuna, T. Awasaki, H. Oda, S. Tsukita and K. Ito. 2001. An enhanced mutant of red fluorescent protein DsRed for double labeling and developmental timer of neural fiber bundle formation. *Journal of Biological Chemistry* 276: 29621–29624.

"Light-inducible fluorescence": since the red fluorescence of scubRFP can be induced by exposure to UV-A light, it is possible to use this protein as a light-inducible reporter. Such a reporter can be used for studying molecular dynamics, in a way that is analogous to FRAP (see above). A small area can be irradiated by the fluorescence-inducing light, after which the process of redistribution of active fluorescent molecules from the irradiated spot can be followed.

REFERENCES

1. Ando, R., H. Hama, M. Yamamoto-Hino, H. Mizuno and A. Miyawaki. 2002. An optical marker based on the UV-induced green-to-red photoconversion of a fluorescent protein. Proceedings of the National Academy of Sciences of the United States of America 99: 12651–12656.
2. Patterson, G. H. and J. Lippincott-Schwartz. 2002. A photoactivatable GFP for selective photolabeling of proteins and cells. *Science* 297: 1873–1877.
3. Chudakov, D. M., V. V. Belousov, A. G. Zaraisky, V. V. Novoselov, D. B. Staroverov, D. B. Zorov, S. Lukyanov and K. A. Lukyanov. 2003. Kindling fluorescent proteins for precise in vivo photolabeling (vol 21, pg 191, 2003). *Nature Biotechnology* 21: 452—452.

Coloring of biological objects for decorative and other non-scientific purposes. Examples: producing decorative fish for aquariums; coloring of fur, wool and milk by means of genetic modifications of appropriate animals; and coloring of decorative plants. Such uses can be implemented by a person skilled in the art having the benefit of the teachings of the current disclosure.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Bacterial Expression Construct

As illustrated in FIG. 1, to prepare a bacterial expression construct, the ORF of the target detectable protein can be amplified by means of polymerase chain reaction (PCR), using primers corresponding to the beginning and end of the protein's ORF. The upstream primer can carry a 5'-heel ttgattgattgaaggagaaatatcATG (SEQ ID NO:1), which encodes three termination codons in three frames (bold), followed by the ribosome binding site (underlined), 6 spacer bases and initiation ATG codon.

The downstream primer can encode a 6×His tag in place of the original termination codon (the heel sequence can be 5'-tta tta gtg atg gtg atg gtg atg (SEQ ID NO:2)), to facilitate protein purification by means of metal-affinity chromatography.

The products of amplification can be cloned into pGEM-T vector (Promega) using manufacturer-provided reagents and protocol. The expressing clones can be identified after overnight growth of the colonies by their fluorescent appearance.

EXAMPLE 2

Excitation and Emission Spectra of the Detectable Proteins

The excitation spectra were measured from the proteins purified after bacterial expression. The spectra are shown in FIGS. 2–21. Emission spectra (dotted lines) were measured using USB2000 uv-vis spectrometer (Ocean Optics), excitation spectra (solid lines)—using spectrofluorometer LS-50B (Perkin Elmer). The indicated positions of excitation and emission maxima are accurate within 5 nm.

EXAMPLE 3

Multiple Marker Constructs

There are several advantages associated with the use of fusion markers, including: 1) achievement of combined functionalities in a single transcription unit, 2) reduced usage of genetic elements, such as promoters and terminators, for expressing multiple marker genes, 3) reduced overall length of insertion sequences that may lead to increased transformation efficiency, and most importantly 4) elimination of molecular interactions between adjacent genetic elements. Such unwanted interactions are frequently encountered when multiple expression units associated with different marker genes are used simultaneously and often complicate the interpretation of expression results.

In an effort to improve marker functionality and versatility, several translational fusions between two genetic markers have been developed. Datla et al. (1991; U.S. Pat. No. 5,639,663) created a bifunctional fusion between GUS and neomycin phosphotransferase (NPTII) to provide a biochemically assayable reporter activity and a conditionally selectable growth advantage for use in plant transformation. Another bifunctional fusion, between GUS and GFP, was also developed to provide both indicative and assayable reporter activities for monitoring transient and stable transgene expression in plant cells (Quaedvlieg et al., 1998). More recently, Li et al. (2001) constructed a bifunctional fusion between GFP and NPTII and successfully used this marker for continuous analysis of promoter activity and transgene expression in transgenic grape plants throughout the entire process of plant development.

Small portions of a protein that provide unique functions such as protein/DNA/substrate binding activity can be inserted into another heterologous protein to create a hybrid fusion with enhanced functionality and utility. In other cases, an entire gene or protein of interest has been fused in-frame to another heterologous gene or protein to form a double fusion to provide combined functionalities. Production of multiple proteins using fusion constructs composed of two genes from transgenic plants has been demonstrated previously (U.S. Pat. No. 6,455,759).

In one embodiment, the subject invention provides cells transformed with a polynucleotide of the present invention comprising an in-frame fusion of nucleotide sequences encoding multiple markers. Preferably, the polynucleotide sequence is provided in an expression construct of the invention. The transformed cell can be a prokaryotic cell, for example, a bacterial cell such as E. coli or B. subtilis, or the transformed cell can be a eukaryotic cell, for example, a plant or animal cell. Animal cells include human cells, mammalian cells, avian cells, fish cells and insect cells. Mammalian cells include, but are not limited to, COS, 3T3, and CHO cells.

Genetic markers that can be used in conjunction with the detectable proteins of the present invention are known in the art and include, for example, polynucleotides encoding proteins that confer a conditionally selective growth advantage, such as antibiotic resistance and herbicide-resistance; polynucleotides encoding proteins that confer a biochemically assayable reporter activity; and polynucleotides encoding proteins that confer an indicative reporter activity. Examples of polynucleotides encoding proteins providing antibiotic resistance include those that can provide for resistance to one or more of the following antibiotics: hygromycin, kanamycin, bleomycin, G418, streptomycin, paromomycin, and spectinomycin. Kanamycin resistance can be provided by neomycin phosphotransferase (NPTII). Examples of polynucleotides encoding proteins providing herbicide resistance include those that can provide for resistance to phosphinothricin acetyltransferase or glyphosate. Examples of genetic markers that confer assayable or indicative reporters activity that can be used in the present invention include, but are not limited to, polynucleotides encoding β-glucuronidase (GUS), β-galactosidase, chloramphenicol acetyltransferase (CAT), luciferase, nopaline synthase (NOS), and green fluorescence protein (GFP).

It should be understood that the examples and embodiments described herein are for illustrative purposes only and that various modifications or changes in light thereof will be suggested to persons skilled in the art and are to be included within the spirit and purview of this application.

We claim:

1. An isolated protein comprising an amino sequence set forth as SEQ ID NO:35 and a variant of said sequence, wherein the amino acid sequence of the variant is at least 95% identical to SEQ ID NO:35 and wherein said variant has emission and excitation maxima that are within +10 nm of the emission and excitation maxima for SEQ ID NO:35.

2. The protein, according to claim 1, wherein said protein has an amino acid sequence set forth as SEQ ID NO:35.

* * * * *